US008440194B2

(12) United States Patent
Zeldis

(10) Patent No.: US 8,440,194 B2
(45) Date of Patent: *May 14, 2013

(54) METHODS USING 3-(4-AMINO-1-OXO-1,3-DIHYDRO-ISOINDOL-2-YL)-PIPERIDINE-2,6-DIONE FOR TREATMENT OF CERTAIN LEUKEMIAS

(75) Inventor: Jerome B. Zeldis, Princeton, NJ (US)

(73) Assignee: Celgene Corporation, Summit, NJ (US)

( * ) Notice: Subject to any disclaimer, the term of this patent is extended or adjusted under 35 U.S.C. 154(b) by 1357 days.

This patent is subject to a terminal disclaimer.

(21) Appl. No.: 12/070,451

(22) Filed: Feb. 19, 2008

(65) Prior Publication Data
US 2008/0145368 A1  Jun. 19, 2008

Related U.S. Application Data

(63) Continuation of application No. 11/244,117, filed on Oct. 4, 2005, now Pat. No. 7,393,862, which is a continuation-in-part of application No. 10/438,213, filed on May 15, 2003, now Pat. No. 7,968,569.

(60) Provisional application No. 60/380,842, filed on May 17, 2002, provisional application No. 60/424,600, filed on Nov. 6, 2002.

(51) Int. Cl.
*A61K 39/395* (2006.01)
*A61K 31/70* (2006.01)
*A61K 31/445* (2006.01)
*A01N 43/04* (2006.01)
*A01N 43/40* (2006.01)

(52) U.S. Cl.
USPC ........ 424/141.1; 424/130.1; 514/47; 514/323

(58) Field of Classification Search ............... 424/141.1, 424/130.1; 514/2, 47, 323
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,810,643 A | 3/1989 | Souza | |
| 4,999,291 A | 3/1991 | Souza | |
| 5,059,595 A | 10/1991 | Le Grazie | |
| 5,073,543 A | 12/1991 | Marshall et al. | |
| 5,120,548 A | 6/1992 | McClelland et al. | |
| 5,134,127 A | 7/1992 | Stella et al. | |
| 5,229,496 A | 7/1993 | Deeley et al. | |
| 5,354,556 A | 10/1994 | Sparks et al. | |
| 5,385,901 A | 1/1995 | Kaplan et al. | |
| 5,391,485 A | 2/1995 | Deeley et al. | |
| 5,393,870 A | 2/1995 | Deeley et al. | |
| 5,528,823 A | 6/1996 | Rudy, Jr. et al. | |
| 5,580,755 A | 12/1996 | Souza | |
| 5,591,767 A | 1/1997 | Mohr et al. | |
| 5,593,990 A | 1/1997 | D'Amato | |
| 5,629,327 A | 5/1997 | D'Amato | |
| 5,635,517 A * | 6/1997 | Muller et al. ................. | 514/323 |
| 5,639,476 A | 6/1997 | Oshlack et al. | |
| 5,674,533 A | 10/1997 | Santus et al. | |
| 5,698,579 A | 12/1997 | Muller | |
| 5,712,291 A | 1/1998 | D'Amato | |
| 5,731,325 A | 3/1998 | Andrulis, Jr. et al. | |
| 5,733,566 A | 3/1998 | Lewis | |
| 5,798,368 A | 8/1998 | Muller et al. | |
| 5,874,448 A | 2/1999 | Muller et al. | |
| 5,877,200 A | 3/1999 | Muller | |
| 5,919,813 A * | 7/1999 | de Juan, Jr. ................... | 514/432 |
| 5,929,117 A | 7/1999 | Muller et al. | |
| 5,955,476 A | 9/1999 | Muller et al. | |
| 6,020,358 A | 2/2000 | Muller et al. | |
| 6,071,948 A | 6/2000 | D'Amato | |
| 6,077,822 A | 6/2000 | Dyrsting et al. | |
| 6,114,355 A | 9/2000 | D'Amato | |
| 6,140,346 A | 10/2000 | Andrulis, Jr. et al. | |
| 6,228,879 B1 | 5/2001 | Green et al. | |
| 6,235,756 B1 | 5/2001 | D'Amato | |
| 6,281,230 B1 | 8/2001 | Muller et al. | |
| 6,316,471 B1 | 11/2001 | Muller et al. | |
| 6,326,388 B1 | 12/2001 | Man et al. | |

(Continued)

FOREIGN PATENT DOCUMENTS

| WO | WO 92/14455 | 9/1992 |
|---|---|---|
| WO | WO 94/20085 | 9/1994 |

(Continued)

OTHER PUBLICATIONS

Alfred Burger, Isosterism and Bioisosterism in Drug Design, in Progress in Drug Research 287-328 (Ernst Jucker, ed., Birkhauser Verlag, 1991).*
George Patani & Edmond LaVoie, Bioisosterism: A Rational Approach in Drug Design, 96 Chem. Rev. 3147 (1996).*
Holger Schulz, et al, Phase 2 Study of a Combined Immunochemotherapy Using Rituximab and Fludarabine in Patients with Chronic Lymphocytic Leukemia, 100 Blood 3115 (2002).*
Z.S. Pavletic, et al, High Incidence of relapse After Autologous Stem-Cell Transplantation for B-cell Chronic Lymphocytic Leukemia or Small Lymphocytic Lymphoma, 9 Ann. Oncol. 1023 (1998).*

(Continued)

*Primary Examiner* — Sean Basquill
(74) *Attorney, Agent, or Firm* — Jones Day

(57) ABSTRACT

Methods of treating, preventing or managing leukemias are disclosed. The methods encompass the administration of an immunomodulatory compound of the invention known as Revlimid® or lenalidomide. The invention further relates to methods of treatment using this compound with chemotherapy, radiation therapy, hormonal therapy, biological therapy or immunotherapy. Pharmaceutical compositions and single unit dosage forms suitable for use in the methods of the invention are also disclosed.

22 Claims, 1 Drawing Sheet

U.S. PATENT DOCUMENTS

| | | | |
|---|---|---|---|
| 6,335,349 B1 | 1/2002 | Muller et al. | |
| 6,380,239 B1 | 4/2002 | Muller et al. | |
| 6,395,754 B1 | 5/2002 | Muller et al. | |
| 6,403,613 B1 | 6/2002 | Man et al. | |
| 6,420,414 B1 | 7/2002 | D'Amato | |
| 6,458,810 B1 | 10/2002 | Muller et al. | |
| 6,469,045 B1 | 10/2002 | D'Amato | |
| 6,476,052 B1 | 11/2002 | Muller et al. | |
| 6,518,298 B2 | 2/2003 | Green et al. | |
| 6,555,554 B2 | 4/2003 | Muller et al. | |
| 6,673,828 B1 | 1/2004 | Green et al. | |
| 6,846,476 B2 | 1/2005 | White | |
| 7,119,106 B2 | 10/2006 | Muller et al. | |
| 7,189,740 B2 | 3/2007 | Zeldis | |
| 7,189,746 B2 * | 3/2007 | Weinstein | 514/364 |
| 7,323,479 B2 | 1/2008 | Zeldis | |
| 7,393,862 B2 * | 7/2008 | Zeldis | 514/320 |
| 7,435,745 B2 | 10/2008 | D'Amato | |
| 7,468,363 B2 | 12/2008 | Zeldis | |
| 7,968,569 B2 | 6/2011 | Zeldis | |
| 8,143,283 B1 * | 3/2012 | D'Amato | 514/323 |
| 2001/0018445 A1 | 8/2001 | Huang et al. | |
| 2001/0022973 A1 | 9/2001 | Ortyl et al. | |
| 2001/0056114 A1 | 12/2001 | D'Amato | |
| 2002/0035090 A1 | 3/2002 | Zeldis et al. | |
| 2002/0045643 A1 | 4/2002 | Muller et al. | |
| 2002/0052398 A1 | 5/2002 | D'Amato | |
| 2002/0054899 A1 | 5/2002 | Zeldis | |
| 2002/0061923 A1 | 5/2002 | D'Amato | |
| 2002/0128228 A1 | 9/2002 | Hwu | |
| 2002/0161023 A1 | 10/2002 | D'Amato | |
| 2002/0173658 A1 | 11/2002 | Muller et al. | |
| 2002/0183360 A1 | 12/2002 | Muller et al. | |
| 2003/0013739 A1 | 1/2003 | Masferrer et al. | |
| 2003/0028028 A1 | 2/2003 | Man et al. | |
| 2003/0045552 A1 | 3/2003 | Robarge et al. | |
| 2003/0069428 A1 | 4/2003 | Muller et al. | |
| 2003/0096841 A1 | 5/2003 | Robarge et al. | |
| 2003/0139451 A1 | 7/2003 | Shah et al. | |
| 2003/0144325 A1 | 7/2003 | Muller et al. | |
| 2003/0181428 A1 | 9/2003 | Green et al. | |
| 2003/0187024 A1 | 10/2003 | D'Amato | |
| 2003/0191098 A1 | 10/2003 | D'Amato | |
| 2003/0235909 A1 | 12/2003 | Hariri et al. | |
| 2004/0029832 A1 | 2/2004 | Zeldis | |
| 2004/0067953 A1 | 4/2004 | Stein et al. | |
| 2004/0077685 A1 | 4/2004 | Figg et al. | |
| 2004/0077686 A1 | 4/2004 | Dannenberg et al. | |
| 2004/0087546 A1 | 5/2004 | Zeldis | |
| 2004/0091455 A1 | 5/2004 | Zeldis | |
| 2004/0122052 A1 | 6/2004 | Muller et al. | |
| 2004/0127545 A1 | 7/2004 | D'Amato et al. | |
| 2004/0147558 A1 | 7/2004 | Treston et al. | |
| 2004/0266809 A1 | 12/2004 | Emanuel et al. | |
| 2005/0049265 A1 | 3/2005 | Adams | |
| 2006/0270837 A1 | 11/2006 | Salcedo et al. | |
| 2008/0292583 A1 | 11/2008 | Zeldis | |
| 2008/0317708 A1 | 12/2008 | Zeldis | |
| 2009/0155265 A1 | 6/2009 | Zeldis | |
| 2010/0093683 A1 | 4/2010 | Zeldis | |
| 2010/0099711 A1 | 4/2010 | Zeldis | |
| 2010/0196369 A1 | 8/2010 | Zeldis | |
| 2010/0260719 A1 | 10/2010 | Zeldis | |
| 2010/0278779 A1 * | 11/2010 | Zeldis | 424/85.2 |
| 2012/0035145 A1 | 2/2012 | Zeldis | |

FOREIGN PATENT DOCUMENTS

| | | | |
|---|---|---|---|
| WO | WO9803502 | 1/1998 | |
| WO | WO 98/54170 | 12/1998 | |
| WO | WO 01/70275 | 9/2001 | |
| WO | WO 01/087307 | 11/2001 | |
| WO | WO 02/15926 | 2/2002 | |
| WO | WO 02/059106 | 8/2002 | |
| WO | WO02/059106 | * 8/2002 | |
| WO | WO 02/064083 | 8/2002 | |
| WO | PCT/US03/11578 | 4/2003 | |
| WO | WO 03/086373 | 10/2003 | |
| WO | WO03/097052 | * 11/2003 | |
| WO | WO 03/099007 | 12/2003 | |
| WO | WO 2004/103274 | 12/2004 | |

OTHER PUBLICATIONS

Seung Tae Lee, et al, Idarubicin, Cytarabine, and Topotecan in Patients With refractory or Relapsed Acute Myelogenous Leukemia and High-Risk Myelodysplastic Syndrome, 68 Am. J Hematol. 237 (2001).*

MJ Keating, et al, Fludarabine: A New Agent with Major Activity Against chronic Lymphocytic Leukemia, 74 Blood 19 (1989).*

Susan O'Brien, et al, Rituximab Dose-Escalation Trial in Chronic Lymphocytic Leukemia, 19 J Clin. Oncol. 2165 (Apr. 15, 2001).*

Judith Karp, et al, Clinical and Biologic activity of the Farnesyltransferase Inhibitor R11577 in Adults with Refractory and relapsed Acute Leukemias: A Phase 1 Clinical Laboratory Correlative Trial, 97 Blood 3361 (2001).*

Roger Herzig, et al, High-Dose Cytosine Arabinoside Therapy for Refractory Leukemia, 62 Blood 361 (1983).*

Biophysical Data Tables.*

Chanan-Khan et al., "Antileukemic effects of lenalidomide (Revlimid®) in patients with relapsed or refractory chronic lymphocytic leukemia: results of a pilot phase II study," *Leukemia & Lymphoma*, 2005, 46(supp 1):S96-S97.

Official Action in corresponding Canadian Patent Application No. 2,570,755 dated Dec. 11, 2009.

U.S. Appl. No. 60/499,723, filed Sep. 4, 2003, Markian.

U.S. Appl. No. 60/372,348, filed Apr. 12, 2002, Hariri et al.

U.S. Appl. No. 09/545,654, filed Apr. 10, 2000, D'Amato.

U.S. Appl. No. 09/287,377, filed Apr. 7, 1999, D'Amato.

U.S. Appl. No. 10/732,867, filed Dec. 9, 2003, D'Amato et al.

Alexanian et al., 2004, "VTD (Velcade, thalidomide, dexamethasone) as primary therapy for newly-diagnosed multiple myeloma," Am. Soc. Hematol. 46th Ann. Meeting Dec. 4-7, 2004, San Diego, CA Abstract #210.

Anderson, 2000, "Thalidomide: Therapeutic potential in hematologic malignancies," Seminars in Hematology 37(1 Supp 3): 1-4.

Attal et al., "Maintenance treatment with thalidomide after autologous transplantation for myeloma: First analysis of a prospective randomized study of the Intergroupe Francophone du Myelome (IFM 99 02)," Am. Soc. Hematol. 46th Ann. Meeting Dec. 4-7, 2004, San Diego, CA Abstract #535.

Bach, 1963, "Thalidomide in Cancer Chemotherapy," *The Lancet*, No. 1271, p. 71.

Bach, 1963, "Studies on the Possible Anti-Neoplastic Effect of Thalidomide," *Acta Pathologica Et Microbiologica Scandinavica* 59:491-499.

Bernardeschi et al., 2003, J. Exp. Clin. Cancer Res. 22(4):129-133.

Cartensen, 1995, *Drug Stability: Principles & Practice*, 2$^{nd}$. ed., Marcel Dekker, New York, NY pp. 379-380.

Chaundhry, 1966, *Cancer Research*, "Effect of Prednisolone and Thalidomide on Induced Submandibular Gland Tumors in Hamster," 26(part 1)1884-86.

Corral et al., 1999, "Differential cytokine modulation and T cell activation by two distinct classes of thalidomide analogues that are potent inhibitors of TNF-alpha," J. Immunol. 163(1):380-386.

Corral et al., 1999, "Immunomodulation by thalidomide and thalidomide analogues," Ann. Rheum. Dis. 58(Suppl 1):I107-113.

Craig et al., 1967, "Potential anticancer agents. III. 2-phthalimidoaldehydes and derivatives," Potential Anticancer Agents III 10:1071-1073.

D'Amato et al., 2001, "Mechanism of action of thalidomide and 3-aminothalidomide in multiple myeloma," Semin. Oncol. 28:597-601.

D'Amato et al., 1994, "Thalidomide is an Inhibitor of Angiogenesis", Proc. Natl. Acad. Sci. 91:4082-4085.

Davies et al., 2001, "Thalidomide and immunomodulatory derivatives augment natural killer cell cytotoxicity in multiple myeloma," Blood 98(1):210-216.

De et al., 1976, "Hansch analysis for some antineoplastic glutarimides," J. Indian Chem. Soc. I.III: 825-826.

De et al., 1976, "Possible antineoplastic agents: III. Synthesis of 6-alkyl-2-[4'-methoxyphthalimido] and 6-alkyl-3-[3'-4'-dimethoxyphenyl] glutarimides," J. Indian Chem. Soc. I.III:1122-1125.

Dimopoulos et al., "Primary treatment with pulsed melphalan, dexamethasone, thalidomide (MDT) for symptomatic patients with multiple myeloma ≧75 years of age," Am. Soc. Hematol. 46th Ann. Meeting Dec. 4-7, 2004, San Diego, CA Abstract #1482.

Dipaolo, 1963, "Effect of Thalidomide on a Variety of Transplantable Tumors," *Cancer Chemotherapy Reports* No. 29, p. 99-102.

Dipaolo, 1963, "In vitro Test Systems for Cancer Chemotherapy, II. Correlation of in vitro Inhibition of Dehydrogenase and Growth with in vivo Inhibition of Ehrlich Asoites Tumor," *Proceedings of the Society for Experimental Biology & Medicine*, 114:384-387.

Dipaolo, 1964, "Thalidomide: Effects on Ehrlich Ascites Tumor Cells in vitro" Science 144:1583.

Dredge et al., 2002, "Novel thalidomide analogues display anti-angiogenic activity independently of immunomodulatory effects," Br. J. Cancer 87(10):1166-1172.

Eisen et al., 2000, "Continuous low dose Thalidomide: a phase II study in advanced melanoma, renal cell, ovarian and breast cancer," Br. J. Cancer 82(4):812-817.

Fakhouri et al., 2004, "Thalidomide in patients with multiple myeloma and renal failure," Br. J. Haematol. 125:90-102.

Fenk et al., 2005, "Single-agent thalidomide for treatment of first relapse following high-dose chemotherapy in patients with multiple myeloma," Leukemia 19(1):156-159.

Folkman et al., 1983, "Angiogenesis inhibition and tumor regression caused by heparin or a heparin fragment in the presence of cortisone," Science 221(4612):719-725.

Gershbein, 1991, "The thalidomide analog, EM 12, enhances 1,2-dimethylhydrazine-induction of rat colon adenocarcinomas," Cancer Letters 60: 129-133.

Grabstald et al., 1965, "Clinical experiences with thalidomide in patients with cancer," Clinical Pharmacology and Therapeutics 6:298-302.

Gupta et al., 2001, "Adherence of multiple myeloma cells to bone marrow stromal cells upregulates vascular endothelial growth factor secretion: therapeutic applications," Leukemia 15(12):1950-1961.

Haslett et al., 2003, "Thalidomide and a thalidomide analogue drug costimulate virus-specific CD8+ T cells in vitro," J. Infect. Dis. 187(6):946-955.

He et al., 1993, "Synthesis of thalidomide analogs and their biological potential for treatment of graft versus host disease (GVHD)," 206th Am. Chem. Soc. Natl. Meet. Chicago, IL Med Chem.

Hideshima et al., 2000, "Thalidomide and its analogs overcome drug resistance of human multiple myeloma cells to conventional therapy," Blood 96(9):2943-2950.

Jonsson. 1972, "Chemical Structure and Teratogenic Properties," Acta Pharm., pp. 521-542.

Lentzsch et al., 2003, "Immunomodulatory analogs of thalidomide inhibit growth of Hs Sultan cells and angiogenesis in vivo," Leukemia 17(1):41-44.

Lentzsch et al., 2002, "S-3-amino-phthalimido-glutarimide inhibits angiogenesis and growth of B-cell neoplasias in mice", Cancer Research 62:2300-2305.

Mauad, 1963, "Clinical Improvements Obtained in Advanced Caner Patients with Treatment with Thalidomide Associated with Hormones," Anais *Paulistas de Medicina e Cirurgia* 86:13-40.

Miyachi et al., 1997, "Novel biological response modifiers: phthalimides with tumor necrosis factor-alpha production-regulating activity," J. Med. Chem. 40:2858-2865.

Muller et al., 1999, "Amino-substituted thalidomide analogs: potent inhibitors of TNF-alpha production," Bioorg. Med. Chem. Lett. 9(11):1625-1630.

Muller et al., 1998, "Thalidomide analogs and PDE4 inhibition," Bioorg. Med. Chem. Lett. 8(19):2669-2674.

Muller et al., 1996, "Structural modifications of thalidomide produce analogs with enhanced tumor necrosis factor inhibitory activity," J. Med. Chem. 39(17):3238-3240.

Offidani et al., 2003, Thalidomide plus oral melphalan for advanced multiple myeloma: a phase II study. Haematologica. Dec. 2003;88(12):1432-1433.

Olson et al., 1965, "Thalidomide (N-phthaloylglutamimide) in the treatment of advanced cancer," Clinical Pharmacology and Therapeutics 6(3):292-297.

Palumbo et al., "A prospective randomized trial of oral melphalan prednisone, thalidomide (MPT) vs. oral melphalan, prednisone (MP): An interim analysis," Am. Soc. Hematol. 46th Ann. Meeting Dec. 4-7, 2004, San Diego, CA Abstract #207.

Penichet et al., 2001, "Antibody-cytokine fusion proteins for the therapy of cancer," J. Immunol. Methods 248(1-2):91-101.

*Physician's Desk Reference*, 2002, 56th ed., pp. 1755-1760.

Raje et al., 1999, "Thalidomide—a revival story," N. Engl. J. Med. 341(21):1606-1609.

Rajkumar et al., "Thalidomide plus dexamethasone versus dexamethasone alone in newly diagnosed multiple myeloma (E1A00): Results of a phase III trial coordinated by the Eastern Cooperative Oncology Group," Am. Soc. Hematol. 46th Ann. Meeting Dec. 4-7, 2004, San Diego, CA Abstract #205.

Rajkumar et al., 2000, "Prognostic value of bone marrow angiogenesis in multiple myeloma," Clin. Cancer Res. 6(8):3111-3116.

Raza et al., 2001, "Thalidomide produces transfusion independence in long-standing refractory anemias of patients with myelodysplatic syndromes," Blood 98(4):958-965.

Ribatti et al., 1999, "Bone marrow angiogenesis and mast cell density increase simultaneously with progression of human multiple myeloma," Br. J. Cancer 79(3-4):451-455.

Roe and Mitchley, 1963, "Thalidomide and Neoplasia" *Nature* 200:1016-1017.

Rowland et al., 2001, "Differential effect of thalidomide and dexamethasone on the transcription factor NF-□B," Intl. Immunopharmacol. 1:49-61.

Rowland et al., 1999, "Selective down-regulation of T cell- and non-T cell-derived tumour necrosis factor by thalidomide: comparisons with dexamethasone," Immunol Lett. 68:325-332.

Rowland et al., 1998, "Differential regulation by thalidomide and dexamethasone of cytokine expression in human peripheral blood mononuclear cells," Immunopharmacol. 40:11-20.

Shah et al., 1999, "Synthesis and enantiomeric separation of 2-phthalimidino-glutaric acid analogues: potent inhibitors of tumor metastasis," J. Med. Chem. 42:3014-3017.

Shibata et al., 1995, "N-alkylphthalimides: structural requirement of thalidomidal action on 12-0-tetradecanoylphorbol-13-acetate-induced tumor necrosis factor a production by human leukemia HL-60 cells," Chem. Pharm. Bull. 43(1):177-179.

Shimazawa et al., 1999, "Antiangiogenic activity of tumor necrosis factor-alpha production regulators derived from thalidomide," Biol. Pharm. Bull. 22(2):224-226.

Singhal et al., 1999, Antitumor activity of thalidomide in refractory multiple myeloma, N. Engl. J. Med. 341(21):1565-1571.

Steins et al., 2002, "Efficacy and safety of thalidomide in patients with acute myeloid leukemia," Blood 99(3):834-839.

Stockdale, 1998, *Medicine*, Rubenstein and Federman, eds., vol. 3, Ch. 12, Sections IV and X.

Ural et al., 2003, "The bisphosphonate zoledronic acid induces cytotoxicity in human melanoma cell lines with enhancing effects of dexamethasone and thalidomide," Int. J. Hematol. 78:443-449.

Vacca et al., 1999, "Bone marrow neovascularization, plasma cell angiogenic potential, and matrix metalloproteinase-2 secretion parallel progression of human multiple myeloma," Blood 93(9):3064-3073.

Wilen et al., 1977, Tetrahedron 33:2725.

Wilen, 1972, *Tables of Resolving Agents and Optical Resolutions*, E.L. Eliel, ed., Univ. of Notre Dame Press, Notre Dame, IN pp. 268.

Wohrer et al., 2004, "Effective treatment of primary plasma cell leukemia with thalidomide and dexamethasone—a case report," Hematol. J. 5(4):361-363.

Wolff ed., 1995, *Burger's Medicinal Chemistry and Drug Discovery*, 5th ed.., pp. 172-178, 949-982.

Anderson, "Moving disease biology from the laboratory to the clinic," *Seminars in Oncology*, 2002 29:17-20.

Barlogie et al., "Total Therapy II (TTII) for newly diagnosed multiple myeloma (MM): preliminary data on feasibility and efficacy in the first 231 enrolled patients; comparison with predecessor trial total therapy I ((TTI) (N=231)," *Blood, Abstract # 2857*, Dec. 7-11, 2001, American Society of Hematology.

Barlogie et al., "High-dose therapy immunomodulatory drugs in multiple myeloma," *Seminars in Oncology*, 2002, 29 (6):26-33.

Barlogie et al., "Introduction: Thalidomide and the IMiDs in multiple myeloma," *Seminars in Hematology*, 2003, 40 (4):1-2.

Barlogie, "Thalidomide and CC-5013 in Multiple Myeloma: The University of Arkansas experience," *Seminars in Hematology*, 2003, 40 (4):33-38.

Bartlett et al., "The evolution of thalidomide and its IMiD derivatives as anticancer agents," *Nature Reviews Cancer*, 2004, 4 (4):1-9.

Bartlett et al., "Phase I study to determine the safety, tolerability and immunostimulatory activity of thalidomide analogue CC-5013 in patients with metastatic malignant melanoma and other advanced cancers," *British Journal of Cancer*, 2004, 90:955-961.

Battegay, "Angiogenesis: mechanistic insights, neovascular diseases, and therapeutic prospects," *J. Mol. Med.*, 1995, 73:333-346.

Baz et al., "Doxil (D), vincristine (V), reduced frequency dexamethasone (d) and revlimid (R) (DVd-R) results in a high response rate in patients with refractory multiple myeloma (RMM)," *Blood, Abstract # 2559, American Society of Hematology*, Dec. 10-13, 2005.

Brennen et al., "Thalidomide and analogues: current proposed mechanisms and therapeutic usage," *Clinical Prostate Cancer*, 2004, 3 (1):54-61.

Celgene Corporation, "Celgene advances immunomodulatory drug (IMiD™) clinical program," Press Release, Feb. 2000.

Celgene Corporation, "Initial Phase I solid tumor data on Celgene's lead IMiD™, Revimid™," Press Release, Jun. 2001.

Celgene Corporation, "Celgene Corporation receives orphan drug designation for Revimid™ for multiple myeloma," Press Release, Oct. 2001.

Celgene Corporation, "Celgene Corporation announces third quarter results. Thalomid® (thalidomide) sales increase 24%. Prescriptions up 50%. Enhanced S.T.E.P.S.® launched. Pilot d-MPH data presented," Press Release, Oct. 2001.

Celgene Corporation, "Celgene expands clinical development program for Revimid™. Five additional trials of Revimid initiated in hematological and solid tumor cancers," Press Release, Jun. 2002.

Celgene Corporation, "Celgene Corporation announces third quarter results. THALOMID® (thalidomide) revenue increases 41% to $30.5 million. Pivotal programs for THALOMID and REVIMID™ finalized. Peer-reviewed publications of THALOMID and REVIMID data. First JNK inhibitor advanced to Phase I clinical trial," Press Release, Oct. 2002.

Celgene Corporation, "Blood reports Revimid™ has anti-tumor activity in patients with relapsed and refractory multiple myeloma," Press Release, Nov. 1, 2002.

Celgene Corporation, "Celgene provides update on clinical pipeline. Celgene Announces first target indication for ACTIMID™, CC-8490. SelCID™ program to advance based on results from Phase I/II trial of CC-1088. First JNK inhibitor successfully completes phase I trial," Press Release, Jan. 2003.

Celgene Corporation, "Celgene Corporation announces fourth quarter and full year results for 2002," Press Release, Jan. 2003.

Celgene Corporation, "Celgene receives fast track status from FDA for Revimid™ in multiple myloma," Press Release, Feb. 2003.

Celgene Corporation, "Celgene receives fast track status from FDA for Revimid™ in myelodysplastic sydromes," Press Release, Apr. 2003.

Celgene Corporation, "New Revimid™ clinical data shows potential as novel approach to treating myelodysplastic syndromes (MDS)," Press Release, May 2003.

Celgene Corporation, "Celgene corporation reports strong operating performance in second quarter as total sales increase 100 percent and profits rise," Press Release, Jul. 2003.

Celgene Corporation, "Celgene corporation reports record operating performance in third quarter as total revenue increases 117% and profits rise," Press Release, Oct. 2003.

Celgene Corporation, "Celgene corporation advances ACTIMID™ (CC-4047) into phase II trial for prostate cancer," Press Release, Oct. 2003.

Celgene Corporation, "Additional clinical data presented on Revimid™ in myelodysplastic sydromes at the American Society of Hematology 45th annual meeting," Press Release, Dec. 2003.

Celgene Corporation, "Celgene corporation reviews 2003 achievements and announces 2004 financial outlook," Press Release, Jan. 2004.

Celgene Corporation, "Revlimid™ receives orphan drug designation from the European commission for multiple myeloma," Press Release, Februapf 2004.

Celgene Corporation, "Revlimid™ receives orphan drug designation from the European commission for myelodysplastic sydromes," Press Release, Mar. 2004.

Celgene Corporation, "Celgene corporation reports record operating performance in first quarter with strong revenue growth and profits," Press Release, Apr. 2004.

Celgene Corporation, "Celgene announces plans to stop phase III trials in melanoma due to lack of efficacy," Press Release, Apr. 2004.

Dalgleish, et al., "New thalidomide analogues; anti-cancer, anti-angiogenic and immunostimulatory," *British Journal of Cancer*, 2001, 85 (1)25.

Dalgleish et al., "Thalidomide analogues CC-5013 and CC-4047 induce T cell activation and IL-12 production in patients with both solid tumours and relapsed and refractory multiple myeloma," *British Journal of Cancer*, 2003, 88(Suppl I), S25-S54.

Davies et al., "Thalidomide (Thal) and immunomodulatory derivatives (IMiDs) augment natural killer (NK) cell cytotoxicity in multiple myeloma(MM))," Abstract # 3617, *American Society of Hematology*, Dec. 1-5, 2000.

Davies et al., "Thalidomide (Thal) and immunomodulatory derivatives (IMiDs) augment natural killer (NK) cell cytotoxicity in multiple myeloma~MM)," Abstract # P222, *VIIIth International Myeloma Workshop*, May 4-8, 2001.

Dibbs et al., "Thalidomide and thalidomide analogs suppress TNFα secretion by myocytes," *Abstract # 1284, Circulation*, 1998.

Dimopoulos et al., "Results of thalidomide and IMIDs in multiple myeloma,", *Abstract # P12.1.4, International Multiple Myeloma Workshop*, May 23-27, 2003.

Dimopoulos et al., "Treatment of plasma cell dyscrasias with thalidomide and its derivatives," *Journal of Clinical Oncology*, Dec. 1, 2003, 21 (23)4444-4454.

Dimopoulos et al., "Study of lenalidomide plus dexamethasone versus dexamethasone alone in relapsed or refractory multiple myeloma (MM): Results of a phase 3 Study (MM-010),", *Abstract # 6, American Society of Hematology*, Dec. 10-13, 2005.

Dredge et al., A costimulatory thalidomide analog enhances the partial anti-tumor immunity of an autologous vaccination in a model of colorectal cancer, *Abstract # 491, American Association for Cancer Research*, Apr. 6-10, 2002.

Dredge et al., "Adjuvants and the promotion of Th1-type cytokines in tumour immunotherapy," *Cancer Immunol. Immunother.*, 2002, 51:521-531.

Dredge et al., "Immunological effects of thalidomide and its chemical and functional analogs," *Critical Reviews in Immunology*, 2002, 22 (5&6):425-437.

Dredge et al., "Protective antitumor immunity induced by a costimulatory thalidomide analog in conjunction with whole tumor cell vaccination is mediated by increased Th1-type immunity[1]," *The Journal of Immunology*, 2002, 168:4914-4919.

Dredge et al., "Recent developments in antiangiogenic therapy," *Expert Opin. Biol. Ther.*, 2002, 2 (8):953-966.

Dredge et al., "Angiogenesis inhibitors in cancer therapy," *Current Opinion in Investigational Drugs*, 2003, 4 (6):667-674.

Dredge et al., "Thalidomide analogs as emerging anti-cancer drugs," *Anti-Cancer Drugs*, 2003, 14:331-335.

Fickentscher et al., "Stereochemical properties and teratogenic activity of some tetrahydrophthalimides," *Molecular Pharmacology*, 1976, 13:133-141.

Galustian et al., "Thalidomide-derived immunomodulatory drugs as therapeutic agents," *Expert Opin. Biol. Ther.*, 2004, 4 (12):1-8.

Glaspy et al., "The potential role of thalidomide and thalidomide analogs in melanoma," *Clinical Advances in Hematology & Oncology*, 2004, 1-7.

Hayashi et al., "Mechanisms whereby immunomodulatory analogs of thalidomide augment autologous NK cell anti-myeloma immunity," *Blood*, Abstract #3219, Dec. 6-10, 2002, *American Society of Hematology*.

Helm et al., "Comparative teratological investigation of compounds of structurally and pharmacologically related to thalidomide," *Arzneimittel Forschung/Drug Research*, 1981, 31 (1)941-949.

Hernandez-Illizaliturr et al., "Addition of immunomodulatory drugs CC5013 or CC4047 to rituximab enhances anti-tumor activity in a severe combined immunodeficiency (SCID) mouse lymphoma model," *Abstract # 235, American Society of Hematology*, Dec. 6-9, 2003.

Hideshima et al., "Thalidomide (Thal) and its analogs overcome drug resistance of human multiple myeloma (MM) cells to conventional therapy," *Abstract 1313, American Society of Hematology*, Dec. 1-5, 2000.

Hunt et al., "Markers of endothelial and haemostatic activation in the use of CC-4047, a structural analogue of thalidamide, in relapsed myeloma," *Blood, Abstract # 3216*, Dec. 6-10, 2002, *American Society of Hematology*.

Hussein et al., "Doxil (D), vincristine (V), reduced frequency dexamethasone (d) and Revlimid (DVd-R) a phase I/II trial in advanced relapsed/refractory multiple myeloma (Rmm) patients," *Blood, Abstract #208, American Society of Hematology*, Dec. 4-7, 2004.

Hwu et al., "Thalidomide and its analogues in the treatment of metastatic melanoma," *Chemotherapy Foundation Symposium*, Abstract #44, 2002.

Kyle, "Current therapy of multiple myeloma," *Internal Medicine*, 2002, 41 (3)175-180.

Kyle et al., "Multiple myeloma," *New England Journal of Medicine*, 2004, 351:1860-1873.

Leblanc et al., "Immunomodulatory drug costimulates T cells via the B7-CD28 pathway," *Blood*, 2004, 103:1787-1790, *American Society of Hematology*.

Lentzsch et al., "In vivo activity of thalidomide and immunomodulatory drugs against multiple myeloma," *VIIIth International Myeloma Workshop*, Abstract #P225, May 4-8, 2001.

Lentzsch et al., "Immunomodulatory derivative of thalidomide (IMiD CC-4047) determine the lineage commitment of hematopoietic progenitors by down regulation of GATA-1 and modulation of cytokine secretion," *Abstract # 3073, American Society of Hematology*, Dec. 6-9, 2003.

Lentzsch et al., "Immunomodulatory derivative of thalidomide (IMiD CC-4047) down regulates CAAT/enhancerbindin protein $^\beta$(C/EBP$^\beta$) in multiple myeloma (MM)," *Abstract # 3456, American Society of Hematology*, Dec. 6-9, 2003.

Luzzio et al., "Thalidomide analogues: derivatives of an orphan drug with diverse biological activity," *Expert Opin. Ther. Patents*, 2004, 14 (2):215-229.

Man et al., "α-Fluoro-substituted thalidomide analogues," *Bioorganic & Medicinal Chemistry Letters 13*, 2003, 3415-3417.

Marriott et al., "Immunotherapeutic and antitumour potential of thalidomide analogues," *Expert Opin. Biol. Ther.*, 2001, 1 (4):1-8.

Marriott et al., "New thalidomide analogues; anti-cancer, anti-angiogenic and immunostimulatory," *British Journal of Cancer*, 85:25, Jul. 6, 2001.

Marriott et al., "Thalidomide and its analogues have distinct and opposing effects on TNF-α and TNFR2 during co-stimulation of both CD4$^+$ and CD8$^+$ T cells," *Clin. Exp. Immunol.*, 2002, 130:75-84.

Marriott et al., "A novel subclass of thalidomide analogue with anti-solid tumor activity in which caspase-dependent apoptosis is associated with altered expression of bcl-2 family proteins[1]," *Cancer Research*, 2003, 63:593599.

Marriott et al., "Thalidomide derived immunomodulatory drugs (IMiDs) as potential therapeutic agents," *Current Drug Targets—Immune, Endocrine & Metabolic Disorders*, 2003, 3:181-186.

Masellis et al., "Changes in gene expression in bone marrow mesenchymal progenitor cells as a consequence of IMiD therapy in multiple myeloma patients," *Blood, Abstract # 1548*, Dec. 7-11, 2001, *American Society of Hematology*.

McCarty, "Thalidomide may impede cell migration in primates by down-regulating integrin β-chains: potential therapeutic utility in solid malignancies, proliferative retinopathy, inflammatory disorders, neointimal hyperplasia, and osteoporosis," *Medical Hypotheses*, 1997, 49:123-131.

Mitsiades et al., "Apoptic signaling induced by immunomodulatory thalidomide analogs (Imids) in human multiple myeloma cells: therapeutic implications," *Abstract # 3224*, Dec. 7-11, 2001, *American Society of Hematology*.

Mitsiades et al., "Apoptic signaling induced by immunomodulatory thalidomide analogs in human multiple myeloma cells: therapeutic implications," *Blood*, 2002, 99:4525-4530, *American Society of Hematology*.

Mitsiades et al., "CC-5013 Celgene," *Current Opinion in Investigational Drugs*, 2004, 5 (6):635-647.

Moutouh et al., "Novel immunomodulatory drugs (IMiDs®): A potential, new therapy for β-hemoglobinopathies," *Abstract # 3740, American Society of Hematology*, Dec. 4-7, 2004.

Patten et al., "The early use of the serum free light chain assay in patients with relapsed refractory myeloma receiving treatment with a thalidomide analogue (CC-4047)," *Abstract # 1640, American Society of Hematology*, Dec. 6-9, 2003.

Payvandi et al., "Effects of a thalidomide analog on binding activity of transcription factors and cell cycle progression of multiple myeloma cell lines," *Blood, Abstract #2487*, Dec. 1-5, 2000, *American Society of Hematology*.

Payvandi et al., "The thalidomide analogs IMiDs enhance expression of CD69 stimulatory receptor on natural killer cells," *Abstract # 1793, American Association for Cancer Research*, Mar. 24-28, 2001.

Payvandi et al., "Thaliomide analogs IMiDs inhibit expression of cyclooxygenase-2 in multiple myeloma cell line and LPS stimulated PBMCs," *Blood, Abstract # 2689*, Dec. 7-11, 2001, *American Society of Hematology*.

Payvandi et al., "Thalidomide and IMiDS inhibit microvessel formation from human arterial rings in the absence of human liver microsomes," *Blood*, Abstract # 5046, Dec. 6-10, 2002, *American Society of Hematology*.

Payvandi et al., "CC-5013 inhibits the expression of adhesion molecules ICAM-1 and CD44 and prevents metastasis of B16 F10 mouse melanoma cells in an animal model," *American Society of Clinical Oncology, Abstract # 992*, 2003.

Payvandi et al., "Immunomodulatory drugs inhibit expression of cyclooxygenase-2 from TNF-α, IL-1β, and LPS-stimulated human PBMC in a partially IL-10-dependent manner," *Cellular Immunology*, 2004, 81-88.

Raje et al., "Combination of the mTOR inhibitor rapamycin and CC-5013 has synergistic activity in multiple myeloma," *Blood*, Dec. 15, 2004, 104 (13)4188-4193.

Rajkumar et al., "Combination therapy with lenalidomide plus dexamethasone (Rev/Dex) for newly diagnosed myeloma," *Blood*, Dec. 15, 2005, 106 (13)4050-4053.

Richardson et al., "A Phase 1 study of oral CC5013, an immunomodulatory thalidomide (Thal) derivative, in patients with relapsed and refractory multiple myeloma (MM)," *Blood, Abstract #3225*, Dec. 7-11, 2001, *American Society of Hematology*.

Richardson et al., "Immunomodulatory drug CC-5013 overcomes drug resistance and is well tolerated in patients with relapsed multiple myeloma," *Blood*, 2002 100:3063-3067, *American Society of Hematology*.

Richardson et al., "A multi-center, randomized, phase 2 study to evaluate the efficacy and safety of 2 CDC-5013 dose regimens when used alone or in combination with dexamethasone (Dex) for the treatment of relapsed or refractory multiple myeloma (MM)," *Blood, Abstract # 825, American Society of Hematology*, Dec. 6-9, 2003.

Richardson et al., "Immunomodulatory analogs of thalidomide: an emerging new therapy in myeloma," *Journal of Clinical Oncology*, 2004, 22(16) 3212-3214.

Richardson et al., "A multicenter, single-arm, open-label study to evaluate the efficacy and safety of single-agent lenalidomide in patients with relapsed and refractory multiple myeloma; preliminary results," *10$^{th}$ International Myeloma Workshop*, Apr. 10-14, 2005.

Richardson et al., "Novel biological therapies for the treatment of multiple myeloma," *Best Practice & Research Clinical Haematology*, 2005, 18 (4):619-634.

Richardson et al., "A phase 1 trial of lenalidomide (REVLIMID®) with bortezomib (VELCADE®) in relapsed and refractory multiple myeloma," *Blood*, Abstract # 365, *American Society of Hematology*, Dec. 10-13, 2005.

Rubin et al., "Principles of cancer treatment-1," 2003, 12 ONCO IV 1.

Schafer et al., "Enhancement of cytokine production and AP-1 transcriptional activity in T cells by thalidomide-related immunomodulatory drugs," *Journal of Pharmacology and Experimental Therapeutics*, 2003, 305(3)1222-1232.

Schey et al., "A phase I study of an immunomodulatory thalidomide analog, CC-4047, in relapsed or refractory multiple myeloma," *Journal of Clinical Oncology*, 2004, 22 (16):1-8.

Schey et al., "A phase I study of an immunomodulatory thalidomide analogue (CC4047) in relapse/refractory multiple myeloma," *International Society for Experimental Hematology, Abstract #248*, 2002.

Shaughnessy et al., "Global gene expression analysis shows loss of C-MYC and IL-6 receptor gene mRNA after exposure of myeloma to thalidomide and IMiD," *Abstract # 2485, The American Society of Hematology*, Dec. 15, 2000.

Shire et al., "TNF-α inhibitors and rheumatoid arthritis," *Exp. Opin. Ther. Patents*, 1998, 8 (5):531-544.

Sorbera et al., "CC-5013. Treatment of multiple myeloma. Treatment of Melanoma. Treatment of myelodysplastic syndrome. Angiogenesis inhibitor. TNF-α production inhibitor," *Drugs of the Future*, 2003, 28(5):425-431.

Streetly et al., "Thalidomide analogue CC-4047 is effective in the treatment of patients with relapsed and refractory multiple myeloma (MM) and induces T-cell activation and IL-12 production," *Abstract # 367, International Multiple Myeloma Workshop*, May 23-27, 2003.

Streetly et al., "Changes in neutrophil phenotype following the administration of CC-4047 (Actimid) to patients with multiple myeloma," *Abstract # 2543, American Society of Hematology*, Dec. 6-9, 2003.

Streetly et al., "An update of the use and outcomes of the new immunomodulatory agent CC-4047 (Actimid) in patients with relapsed/refractory myeloma," *Abstract #829, American Society of Hematology*, Dec. 6-9, 2003.

Teo et al., "A phase 1, single-blind, placebo-controlled, ascending single oral dose, safety, tolerability and pharmacokinetic study of CDC-501, a novel immunomodulatory- oncologic agent, in healthy male subjects with a comparison of fed and fasted," *Clinical Pharmacology and Therapeutics*, 2002, 71 (2)93.

Teo et al., "Chiral inversion of the second generation IMiD™ CC-4047 (ACTIMID™) in human plasma and phosphate-buffered saline," *Chirality*, 2003, 15:348-351.

Thertulien et al., "Hybrid MEL/DT PACE autotransplant regimen for Multiple Myeloma (MM)—safety and efficacy data in pilot study of 15 patients," *Blood, Abstract # 2869, American Society of Hematology*, Dec. 7-11, 2001.

Tohnya et al., "A phase I study of oral CC-5013 (lenalidomide, Revlimid™), a thalidomide derivative, in patients with refractory metastatic cancer," *Clinical Prostate Cancer*, 2004, 2:241-243.

Tricot et al., "Angiochemotherapy (ACT) for multiple myloma (MM) with DT-PACE results in a high response rate, but in contrast to tandem transplants with melphalan does not affect durable disease control," *Blood, Abstract # 3531, American Society of Hematology*, Dec. 7-11, 2001.

Tsenova et al., "Use of IMiD3, a thalidomide analog, as an adjunct to therapy for experimental tuberculous meningitis," *Antimicrobial Agents and Chemotherapy*, 2002, 46 (6)1887-1895.

Weber, "Lenalidomide (CC-5013, Revlimid™) and other ImiDs," *Abstract # PL5.02, International Multiple Myeloma Workshop*, Apr. 10-14, 2005.

Weber et al., "A multicenter, randomized, parallel-group, double-blind, placebo-controlled study of lenalidomide plus dexamethasone versus dexamethasone alone in previously treated subjects with multiple myeloma," *Abstract # PO.738, International Multiple Myeloma Workshop*, Apr. 10-14, 2005.

Ye et al., "Novel IMiD drugs enhance expansion and regulate differentiation of human cord blood CD34+ cells with cytokines," *Blood, Abstract #4099, American Society of Hematology*, Dec. 6-10, 2002.

Zangari et al., "Risk factors for deep vein thrombosis (DVT) in a large group of myeloma patients (Pts) treated with thalidomide (Thal): The Arkansas Experience," *Blood, Abstract # 681, American Society of Hematology*, Dec. 7-11, 2001.

Zangari et al., "Revimid 25 mg (Rev 25)×20 versus 50 mg (Rev 50)×10 q 28 days with bridging of 5 mg×10 versus 10 mg×5 as post-transplant salvage therapy for multiple myeloma (MM)," *Blood, Abstract # 1642, American Society of Hematology*, Dec. 6-9, 2003.

Zeldis et al., "Potential new therapeutics for Waldenstrom's macroglobulinemia," *Seminars in Oncology*, 2003, 30 (2):275-281.

Zhang et al., "CC-5079, a novel microtubule and TNF-a inhibitor with anti-angiogenic and antimetastasis activity," Abstract # B012, *International Conference on Molecular Targets and Cancer Therapeutics*, Nov. 17-21, 2003.

Liu et al., "Phase I study of Cc-5013 (Revimid), a thalidomide derivative, in patients with refractory metastatic cancer," American Society of Clinical Oncology, Abstract #927, 2003.

Zangari et al., "Results of phase I study of CC-5013 for the treatment of multiple myeloma (MM) patients who relapse after high dose chemotherapy (HDCT)," American Society of Hematology, Abstract #3226, 2001.

Zeldis et al., "Update on the evolution of the IMiD™," International Society for Biological Therapy of Cancer, Oral Abstract, 2003.

Database PHARHAML XP002369094 retrieved from STN. Database accession No. 1659300, & Marketletter, Oct. 9, 2001.

Database NLDB XP002369096 retrieved from STN. Database accession no. 2002:35280, & Marketletter, Jun. 18, 2001.

Figg et al., "Inhibition of angiogenesis: treatment options for patients with metastatic prostate cancer," Investigational New Drugs, 2002, 20(2): 183-194.

Anderson, "The Role of Immunomodulatory Drugs in Multiple Myeloma," Seminars in Hematology, vol. 40, No. 4, Suppl 4, 2003: pp. 23-32.

Weber, "Thalidomide and Its Derivatives: New Promise for Multiple Myeloma," Cancer Control, Vo. 10, No. 5, 375-383, 2003.

Chanan-Khan, A.A.; Miller, K.C.; Marshall, P.; Padmanabhan, S.; Brady, W.; Bernstein, Zale P., Wallace, P.; Czuczman, M.S.; *Thalidomide (T) in Combination With Fludarabine (F) as Initial Therapy for Patients With Treatment Naive Chronic Lymphocytic Leukemia (CLL): Preliminary Results of a Phase I/II Clinical Trial.* Abstract #2974, American Soc. of Hematology, Dec. 2005.

Chanan-Khan, A.A.; Padmanabhan, S., Miller, K.C.; Pera, P., Dimiceli, L.; Ersing, N.; Wallace, P.; Rickert, M.; Porter, C.; *In Vivo Evlauation of Immunomodulating Effects of Lenalidomide (L) on Tumor Cell Microenvironment as a Possible Underlying Mechanism of the Antitumor Effects Observed in Patients With Chronic Lymphocytic Leukemia (CLL)*, Abstract #2975, American Soc. of Hematology, Dec. 2005.

Dimiceli, L.; Miller, K.C.; Pera, P., Rickert, M.; Wallace, P.;Marshall, P., Depaolo, Dawn, Padmanabhan, S.; Landrigan, B.; Chanan-Khan, A.A.; *Characterization of IMiDs (Immunomodulating Agents) Induced "Flare Reaction" in Patients With Chronic Lymphocytic Leukemia (CLL) and Correlation with Changes in Serum Cytokine Levels*, Abstract #5049, American Soc. of Hematology, Dec. 2005.

Kay, N.; Geyer, S.; Ismail, Y.; Phyliky, R.; Kutteh, L. Li, C.Y.; *Thalidomide (Td) Treatment in Chronic Lymphocytic Leukemia (CLL): A North Central Cener Treatment Group (NCCTG) Study.* Abstract #5162, American Soc. Of Hematology, Dec. 2003.

Furman, R.R.; Leonard, J.P.; Allen, S.L.; Coleman, M.; Rosenthal, T.; Gabrilov, J.L.; *Thalidomide Alone or in Combination with Fludarabine are Effective Treatments for Patients with Fludarabine-Relapsed and Refractory CLL*. Abstract #6640; American Soc. of Clinical Oncology, May 2005.

Chanan-Khan, A.A.; Miller, K.C.; Dimiceli, L.; Padmanabhan, S.; Lawrence, D.; Bernstein, Z.; Takeshita, K.; Spaner, D. Marshall, P.; Wallace, P.; Byrne, C.; Crystal, C.; Czuczman, M.S.; *Results of a Phase II Study of Lenalidomide (L) {Revlimid®} in Patients with Relapsed or Refractory Chronic Lymphocytic Leukemia CLL. Session Type: Oral Session.* Abstract #447, American Soc. of Hematology, Dec. 2005.

Chanan-Khan, A.A.; Miller, K.C.; Takeshita, K.; Koryzna, A.; Donohue, K.; Bernstein, Z.; Mohr, a.; Klippenstein, D.; Marshall, P.; Zeldis, J.; Berger, Czuczman, M.S.; *Results of a Phase I Clinical*

*Trial of Thalidomide in Combination with Fludarabine as Intial Therapy for Patients with Treatment-Requiring Chronic Lymphocytic Leukemia (CLL)*. Blood, Nov. 15, 2005, vol. 106, No. 10; 3348-3352.
Wechalekar, A.D.; Chen, C.I. Sutton, D.; Reece, D.; Voralia, M.; Stewart, A.K.; Intermediate Dose Thalidomide (200 mg Daily) Has Comparable Efficacy and Less Toxicity than Higher Doses in Relapsed Multiple Myeloma, Leukemia and Lymphoma, 2003, vol. 44(7), pp. 1147-1149.
Steurer, M.; Spizzo, G.; Mitterer, M.; Gastl, G.; *Low-Dose Thalidomide for Multiple Myeloma: Interim Analysis of a Compassionate Use Program*. Onkologie, 2004: 27: pp. 150-154.
Heranandez-Ilizaliturri, F.J.; Reddy N.; Holkava, B.; Ottman, E.; Czuczman, M.S.; *Immunomodulatory Drug CC-5013 or CC-4047 and Rituximab Enhance Antitumor Activity in a Severe Combined Immunodeficient Mouse Lymphoma Model*, Clinical Cancer Research, 2005;11(16) Aug. 15, 2005.
Chanan-Khan, A.A.; Porter C.W.; *Immunomodulating Drugs for Chronic Lymphocytic Leukaemia*, Lancet Oncol. 2006:7:480-88.
Trompeter, S.; S, DS; Yong, K.; Jewell, A.; Nathwani, A.; *Thalidomide in Combination with Dexamethasone and Cyclophosphamide Shows Activity in Patients with Relapsed Chronic Lymphocytic Leukaemia*, 11$^{th}$ International Workshop on Chronic Lymphocytic Leukemia, 2005, Meeting Abstract vol. 46, 88 abstr.
Chanan-Khan, A.; Miller, K.; Marshal, P.; Padmanabhan, S.; Brady, W.; Bernstein, ZP; Czuczman, MS; *Fludarabine in Combination with Thalidomide as Primary Therapy for Patients with Chronic Lymphocytic Leukemia: Preliminary Results of a Phase I/II Clinical Trial*, Leukemia & Lymphoma, Sep. 2005; 46 (suppl 1): S88.
Trompeter, S.; D'Sa, S.; Yong, K.; Jewell, A.; Nathawani, AC; *Thalidomide in Combination with Dexamethasone and Cyclophosphamide Shows Activity in Patients with Relapsed Chronic Lymphocytic Leukaemia*, Leukemia & Lymphoma, Sep. 2005; 46 (suppl 1): S88.
Miller, K.C.; Czuczman, M.S.; Dimicell, L.; McCarthy, P.; Bernstein, P.; Zeldis, J.B.; Mohr, A.; Chanan-Khan, A.A.; *Antileukemic Effects of Novel Immunomodulatory Ageng Lenalinomide (L) with or without Rituximab (R) in Patients (PTS) with Relapsed (rel) or Refractory (ref) Chronic Lymphocytic Leukemia (CLL). Encouraging Preliminary Results of an Ongoing Phase II Clinical Study*, Journal of Clinical Oncology, 2005 ASCO Annual Meeting Proceedings; vol. 23, No. 165 (Jun. 1 Supplement), 2005: 6557.
Mesa, RA; Tefferi, A.; Li, C-Yang; Steensma, DP; *Hematologic and Cytogenetic Response to Lenalidomide Monotherapy in Acute Myeloid Leukemia Arising from JAK2$^{V617F}$ Positive, del(5)(q13q33) Myelodysplastic Syndrome*; Leukemia, 2006; 20, 2063-2064.
Official Action dated Feb. 10, 2009 in JP Application No. 2004-545192. (English translation provided.)
Tsimberidou, A. et al., "Pilot study of recombinant human soluble tumor necrosis factor (TNF) receptor (p75) fusion protein (TNFR:Fe;Enbrcl) in patients with refractory multiple myeloma: increase in plasma TNFα levels during treatment," *Leukemia Research*, 2003, 27:375-380.
Krenn, M. et al., "Improvements in Solubility and Stability of Thalidomide upon Complexation with Hydropropyl-β-Cyclodextrin," *Journal of Pharmaceutical Sciences*, 1992, 8I(7):685-689.
Extracts from drug databases: retrieved from http://www.nextbio.com/b/search/ov/IMiD3%20cpd on Nov. 26, 2010 and http://pubchem.ncbi.nlm.nih.gov/summary/summary.cgi?cid=216326 on Nov. 26, 2010.
Genentech's website located at http://www.gene.com/gene/products/information/oncology/rituxan/index.jsp?hl—en&q=RITUXAN+rituximab retrieved May 16, 2006.
Filella et al., *Cancer Detect. Prev.*, 1996, 20(1), 52-56.
"Celgene Drug Promises Activity in Solid Tumors," *Marketletter*, Jun. 18. 2001.
Kyle et al., "The Application of Thalidomide in Multiple Myeloma," *Semin. Oncol.*, 2001, 28(6), 583-587.
Broder et al., "Dideoxycytidine: Current Clinical Experience and Future Prospects. A Summary," Am. J. Med., 1990, 88(5B), 31S-33S.
Badoux et al., "Lenalidomide as initial therapy of elderly patients with chronic lymphocytic leukemia", *Blood*, 2011, 118(13):3489-3498.

Ferrajoli et al., "The Combination of Lenalidomide and Rituximab Induces Complete and Partial Responses in Patients with Relapsed arid Refractory Chronic Lymphocytic Leukemia", *Blood (ASH Annual Meeting Abstracts)*, 2010, 116: Abstract 1395.
Chen, C. et al., "Single-Agent Lenalidomide in the Treatment of Previously Untreated Chronic Lymphocytic Leukemia," *Journal of Clinical Oncology*, Mar. 20, 2011. 29(9):1175-1181.
Wendtner, C-M. et al., "Final results of a multicenter phase 1 study of lenalidomide in patients with relapsed or refractory chronic lymphoeytic leukemia," *Leukemia & Lymphoma*, Mar. 2012, 53(3):417-423.
European Search Report dated Oct. 16, 2012 in corresponding EP Application No. 12171482.8.
Blum, W. et al., "Dose Escalation of Lenalidomide in Relapsed or Refractory Acute Leukemias," *Journal of Clinical Oncology*, Nov. 20, 2010, 28(33):4919-4925.
Official Action dated Jul. 17, 2012 in JP Application No. 2008-534665 (English translation provided).
Rai, Kanti R. et al., "Fludarabine Compared with Chlorambucil as Primary Therapy for Chronic Lymphocytic Leukemia," *The New England Journal of Medicine*, Dec. 14, 2000, 343(24):1750-1757.
Patt, Y. et al., "Durable Clinical Response of Refractory Hepatocellular Carcinoma to Orally Administered Thalidomide," *American Journal of Clinical Oncology*, 2000, 23(3):319-321.
Richardson, P. et al., "Thalidomide: The Revival of a Drug with Therapeutic Promise in the Treatment of Cancer," *Principles & Practice of Oncology*, 2001, 15(2):1-18.
Thomas, M. and Doss, D., *Thalidomide Nursing Roundtable Update*, Monograph by AAMCE, Sep. 2002.
Richardson, P. et al., "Thalidomide: Emerging Role in Cancer Medicine," *Annual Review of Medicine*, 2002, 53:629-657.
Berenson, J.R. et al., "Initiation and Maintenance of Multiple Myeloma," *Seminars in Hematology*, 1999, 36(1, Supp. 3):9-13.
Gollob, J.A. et al., "Characterization of a Novel Subset of CD8 T Cells That Expands in patients Receiving Interleukin-12," *Am. Soc. For Clin. Investigation, Inc.*, 1998, 102(3):561-575.
Cavanagh, L.L., et al., "Dendritic Epidermal T-Cell Involvement in Induction of CD8+ T-Cell-Mediated Immunity Against an Ultraviolet Radiation-Induced Skin Tumor," *Int. J. Cancer*, 1997, 70(1):98-105.
Thomas, D.A. et al., "Thalidomide as anti-angiogenesis therapy (rx) in refractory or relapsed leukemia,", *American Society of Hematology*, Dec. 3-7, 1999, Abstract #2269.
Barlogie, B. et al., "Anti-Angiochemotherapy Effects CR in Plasma Cell Leukemia and Fulminant Multiple Myeloma (MM)," *American Society of Hematology*, Dec. 4-9, 1998, Abstract #4180.
Hideshima, T., et al., "NF-KB as a Therapeutic Target in Multiple Myeloma (MM)," *American Society of Hematology*, Dec. 7-11, 2001, Abstract #1581.
Lentsch, S. et al., "3-Amino-Phthalimido-Glutarimide (S-3APG) Inhibits Angiogenesis and Growth in Drug Resistant Multiple Myeloma (MM) in vivo," *American Society of Hematology*, Dec. 7-11, 2001, Abs. #1976.
Park, Y., Kim, S.A., Kim, C.J., Chung, J.H., Mechanism of the Effect of Thalidomide on Human Multiple Myeloma Cells. Abstract #2685. American Society of Clinical Oncology, May 12-17, 2001.
Meregalli et al., "High-dose dexamethasone as first line therapy of multiple myeloma?", Recenti Progressi in Medicina, 1998, 89(1):18-20.
Official Action in corresponding Canadian Application No. 2,476,983 dated Aug. 21, 2009.
List, A., "New Approaches to the Treatment of Myelodysplasia," *The Oncologist*, 2002, 7(suppl. 1):39-49.
Kurzrock, R., "Myelodysplastic syndrome overview," *Seminars in Hematology* (Abstract only), 2002, 39(3)(suppl. 2):18-25 Abstract only.
Goerner, et al., "Morbidity and mortality of chronic GVHD after hematopoietic stem cell transplantation from HLA-identical siblings for patients with aplastic or refractory anemias," *Biology of Blood and Marrow Transplantation* (Abstract only), 2002, 8(1):47-56.
Thomas, D., "Pilot studies of Thalidomide in Acute Myelogenous Leukemia, Myelodysplastic Syndromes, and Myeloproliferative Disorders," *Seminars in Hematology*, 2000, 37(1)(suppl. 3):26-34.

Zorat, F. et al., "The clinical and biological effects of thalidomide in patients with myelodysplastic syndromes," *British Journal of Haematology,* 2001, 115:881-894.

Official Action dated Feb. 10, 2009 in JP Application No. 2004-545192. (English translation provided.).

Teramura, M., Men-ekiyokusei Ryouhou, *Current Therapy,* 2000, 18(5):140-144 (in Japanese).

Kon-nichi no Chiryou Shishin, 1997 [Pocket Edition], Igaku Shoin, 1997, 513-514 (in Japanese).

Okamoto, T., Kotsuzuiikeisei Shoukougun to Men-eki Ijo, Bessatsu Nihon Rinsho, Syndrome Series for each area, No. 22, Blood Syndromes III, Nihon Rinshou, 213-216 (in Japanese), Oct. 1998.

Merck Manual, 17th ed. Japanese version, 1999, 951-952.

Notice of Allowance from U.S. Appl. No. 11/096,155 dated Jan. 12, 2010.

Rajkumar et al., "Combination therapy with thalidomide plus dexamethasone for newly diagnosed multiple myeloma," *American Society of Hematology,* 43rd Annual Meeting, Dec. 7-11, 2001, Abstract #3525.

Scheffler et al., "Safety and pharmacokinetics of CDC-501, a novel immunomodulatory-oncologic agent, after single then multiple, oral 100 mg twice daily doses," *American Society for Clinical Pharmacology and Therapeutics,* Mar. 24-27, 2002, Abstract #WPIII-63.

Marriott et al., "Thalidomide analogue CDC-501 is safe and well tolerated by patients with end stage cancer and shows evidence of clinical responses and extensive immune activation," *Br. J. Cancer,* 2002, 86(Supp. 1):Abst 6.4.

Kast, R.E., "Evidence of a mechanism by which etanercept increased TNF-alpha in multiple myeloma: New insights into the biology of TNF-alpha giving new treatment opportunities—the role of burproion," *Leukemia Research,* 2005, 29:1459-1463.

Tsimberidou, A. et al., "Pilot study of recombinant human soluble tumor necrosis factor (TNF) receptor (p75) fusion protein (TNFR:Fc;Enbrcl) in patients with refractory multiple myeloma: increase in plasma TNFα levels during treatment," *Leukemia Research,* 2003, 27:375-380.

Dimopoulos, et al., "Long-term follow-up on overall survival from the MM-009 and MM-010 phase III trials of lenalidomide plus dexamethasone in patients with relapsed or refractory multiple myeloma," *Leukemia,* 2009, 1-6.

Hideshima, T., et al., "A review of lenalidomide in combination with dexathasone for the treatment of multiple myeloma," *Therapeutics and Clinical Risk Management,* 2008, 4(1):129-136.

Wang, M., et al., "Lenalidomide plus dexamethasone is more effective than dexamethasone alone in patients with relapsed or refractory multiple myeloma regardless of prior thalidomide exposure," *Blood,* 2008, 112(12):4445-4451.

Gandhi, A., et al., "Dexamethasone Synergizes with Lenalidomide to Inhibit Multiple Myeloma Tumor Growth, But Reduces Lenalidomide-Induced Immunomodulation of T and NK Cell Function," *Current Cancer Drug Targets,* 2010, 10(1):1-13.

Gay, F. et al., "Lenalidomide plus dexamethasone versus thalidomide plus dexamethasone in newly diagnosed multiple myeloma: a comparative analysis of 411 patients," *Blood,* 2010, 115(97):1343-150.

Richardson, P. et al., "Thalidomide in multiple myeloma," *Biomed Pharmacother,* 2002, 56:115-28.

Swartz, G. et al., "Pre-clinical evaluation of ENMD-0995: A thalidomide analog with activity against multiple myeloma and solid tumors," *Cell and Tumor Biology,* 2002, 43:181-182, Abstract# 910.

Mazucco, R., "Angiogenesis and Anti-angiogenesis Therapeutics," *IDrugs,* 2002, 5(4): 320-322.

Worker, C., "JP Morgan Hambrecht & Quist—20th Annual Healthcare Conference," *IDrugs,* 2002, 5(2):113-116.

Treston, A. et al., "Pre-Clinical Evaluation of a Thalidomide Analog with Activity Against Multiple Myeloma and Solid Tumors—ENMD-0995 (S-(-)-3-(3-amino-phthalimido)-glutarimide)," *Blood,* 2002, 100(11):816a, Abstract #3225.

Mazucco, R. and Williams, L., "Immunotherapy, chemoprevention and angiogenesis," *IDrugs,* 2002, 5(5):408-411.

Fernandes, P., "Anti-Cancer Drug Discovery and Development Summit," *IDrugs,* 2002, 5(8):757-764.

Notification letter dated Aug. 30, 2010 from Natco Pharma limited to Celgene Corporation re: Notification purusant to § 505(j)(2)(B) of the Federal Food, Drug and Cosmetic Act.

Complaint for Patent Infringement filed on Oct. 8, 2010 by Celgene Corporation in the U.S. District Court, District of New Jersey against Natco Pharma Limited.

Answer to Complaint filed on Nov. 18, 2010 by Natco Pharma Limited in the U.S. District Court, District of New Jersey.

Grosshans, E. and Illy, G., "Thalidomide Therapy for Inflammatory Dermatoses," *International Journal of Dermatology,* 1984, 23(9):598-602.

Krenn, M. et al., "Improvements in Solubility and Stability of Thalidomide upon Complexation with Hydropropyl-β-Cyclodextrin," *Journal of Pharmaceutical Sciences,* 1992, 81(7):685-689.

Schmahl, H. J. et al., "Pharmacokinetics of the Teratogenic and Nonteratogenic Thalidomide Analogs EM 12 and Supidimide in the Rat and Marmoset Monkey", in *Pharmacokinetics in Teratogenesis,* CRC Press, 1987, vol. I, Ch. 12, pp. 181-192.

Schumacher, H. et al., "The Teratogenic Activity of a Thalidomide Analogue, $EM_{12}$, in Rabbits, Rats, and Monkeys," *Teratology,* 1971, 5:233-240.

Smith, R. et al., "Studies on the Relationship Between the Chemical Structure and Embryotoxic Activity of Thalidomide and Related Compounds," in *A Symposium on Embryopathic Activity of Drugs,* J. & A. Churchill Ltd., 1965, Session 6, pp. 194-209.

Sheskin, J. and Sagher, F., "Trials with Thalidomide Derivatives in Leprosy Reactions," *Leprosy Review,* 1968, 39(4):203-205.

Sheskin, J., "Study with Nine Thalidomide Derivatives in the Lepra Reaction," *Pharmacology and Therapeutics,* 1978, 17:82-84.

Raje, N. and Anderson, K., "Thalidomide and immunomodulatory drugs as cancer therapy," *Current Opinions in Oncology,* 2002, 14:635-640.

Kumar, S. et al., "Thalidomide as an anti-cancer agent,"*J. Cell. Mod. Med.,* 2002, 6(2):160-174.

Singhal, S. and Mehta, J., "Thalidomide in Cancer," *BioDrugs,* 2001, 15(3):163-172.

Notice of Opposition to EP 1 505 973 filed by Synthon B.V. on Nov. 30, 2010.

Notice of Opposition to EP 1 505 973 tiled by Strawman Limited on Dec. 1, 2010.

Samson, D. et al., "Infusion of Vincristine and Doxorubicin with Oral Dexamethasone as First-Line Therapy for Multiple Myeloma," *The Lancet,* 1989, 334(8668):882-885.

Barlogie, B. et al., "Effective Treatment of Advanced Multiple Myeloma Refractory to Alkylating Agents," *N. Engl. J. Med.,* 1984, 310(21):1353-1356.

Dimopoulos, M. et al., "Thalidomide and dexamethasone combination for refractory multiple myeloma," *Annals of Oncology,* 2001, 12:991-995.

Zangari, M., et al., "Thrombogenic activity of doxorubicin in myeloma patients receiving thalidomide: implications for therapy," *Blood,* 2002, 100:1168-1171.

List, A. et al., "High Erythropoietic Remitting Activity of the Immunomodulatory Thalidomide Analog, CC5013, in Patients with Myelodysplastic Syndrome (MDS)," Abstract #353, *Blood,* 2002, 100(11):96a.

Mufti, G. et al., "Myelodysplastic Syndrome," *American Society of Hematology,* 2003, pp. 176-199.

Extracts from drug databases: retrieved from http://www.nextbio.com/b/search/ov/IMiD3%20cpd on Nov. 26, 2010 and http://pubchem.ncbi.nlm.nih.gov/summary/summary.cgi?cid=216326 on Nov. 26, 2010.

\* cited by examiner

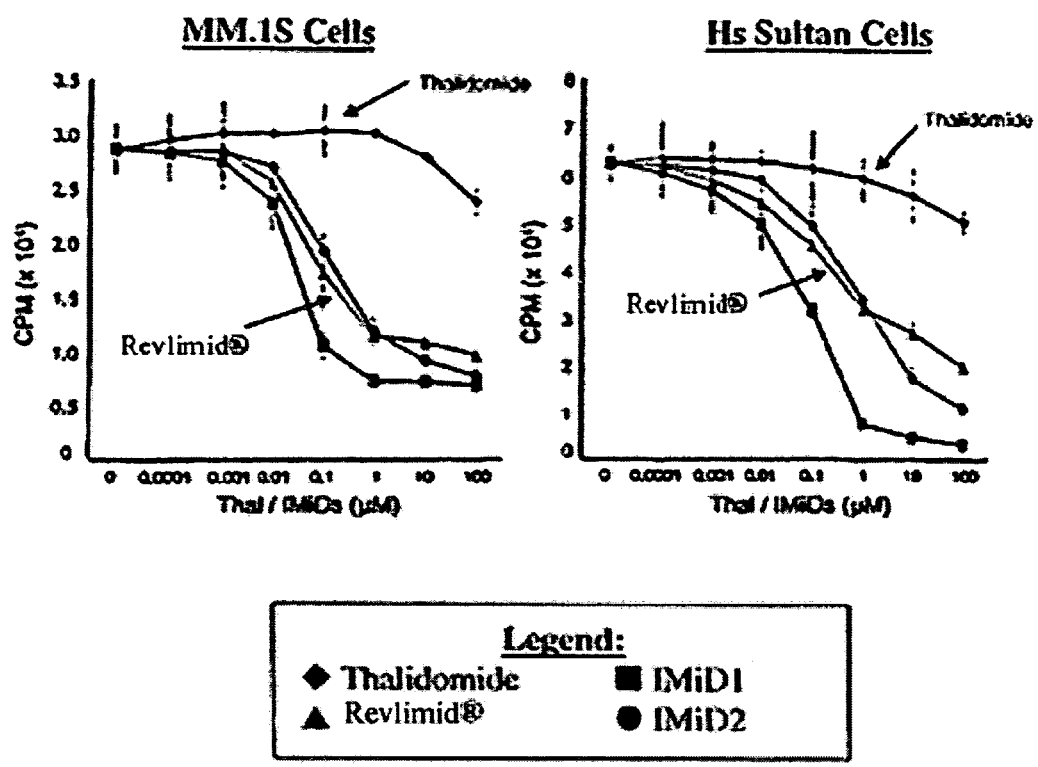

METHODS USING 3-(4-AMINO-1-OXO-1,3-DIHYDRO-ISOINDOL-2-YL)-PIPERIDINE-2,6-DIONE FOR TREATMENT OF CERTAIN LEUKEMIAS

This application is a continuation of U.S. patent application Ser. No. 11/244,117, filed Oct. 4, 2005 now U.S. Pat. No. 7,393,862, which is a continuation-in-part of U.S. patent application Ser. No. 10/438,213, filed May 15, 2003 now U.S. Pat. No. 7,968,569, which claims the benefit of U.S. provisional application Nos. 60/380,842, filed May 17, 2002, and 60/424,600, filed Nov. 6, 2002, the entireties of which are incorporated herein by reference.

1. FIELD OF THE INVENTION

This invention relates to methods of treating, preventing or managing leukemias with an immunomodulatory compound having the chemical name of 3-(4-amino-1-oxo-1,3-dihydro-isoindol-2-yl)-piperidine-2,6-dione, which is also known as Revlimid® or Revimid®. In particular, this invention encompasses methods of treating, preventing or managing leukemias, including but not limited to, chronic lymphocytic leukemia, chronic myelocytic leukemia, acute lymphoblastic leukemia, acute myelogenous leukemia and acute myeloblastic leukemia, using the compound alone as a therapeutic.

The invention also encompasses the use of specific combinations or "cocktails" of Revlimid® and other therapy, e.g., radiation or other chemotherapeutics, including but not limited to, anti-cancer agents, immunosuppressive agents, and anti-inflammatories such as steroids. The invention also relates to pharmaceutical compositions and dosing regimens with said compound alone that is as a therapeutic.

2. BACKGROUND OF THE INVENTION

2.1 Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J. and Kale, D., *Immunology*, 17.1-17.12 (3rd ed., Mosby, St. Louis, Mo., 1993).

There is an enormous variety of cancers which are described in detail in the medical literature. Examples includes cancer of the blood, lung, colon, rectum, prostate, breast, brain, and intestine. The various forms of the cancers such as leukemias are described in U.S. provisional application No. 60/380,842, filed May 17, 2002, the entireties of which are incorporated herein by reference (see, e.g., Section 2.2. Types of Cancers).

In particular, leukemia refers to malignant neoplasms of the blood-forming tissues. Although viruses reportedly cause several forms of leukemia in animals, causes of leukemia in humans are to a large extend unknown. *The Merck Manual*, 944-952 (17th ed. 1999). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. *The Merck Manual*, 946-949 (17th ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or acute myeloblastic leukemia (AML), occurs at all ages and is the more common acute leukemia among adults; it is the form usually associated with irradiation as a causative agent.

Chronic leukemias are described as being lymphocytic (CLL) or myelocytic (CML). *The Merck Manual*, 949-952 (17th ed. 1999). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total WBC count is usually about 200,000/μL, but may reach 1,000,000/μL. CML is relatively easy to diagnose because of the presence of the Philadelphia chromosome.

The incidence of cancer continues to climb as the general population ages, as new cancers develop, and as susceptible populations (e.g., people infected with AIDS or excessively exposed to sunlight) grow. In particular, chronic lymphocytic leukemia is an incurable leukemia with limited therapeutic options for patients with relapsed or refractory disease. A tremendous demand therefore exists for new methods and compositions that can be used to treat patients with cancer including leukemia.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, bFGF).

Accordingly, compounds that can control angiogenesis or inhibit the production of certain cytokines, including TNF-α, may be useful in the treatment and prevention of various cancers.

2.2 Methods of Treating Cancer

Current cancer therapy may involve surgery, chemotherapy, hormonal therapy and/or radiation treatment to eradicate neoplastic cells in a patient (see, for example, Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove refractory to standard chemotherapeutic treatment protocols.

Still, there is a significant need for safe and effective methods of treating, preventing and managing cancer, particularly for diseases that are refractory to standard treatments, such as surgery, radiation therapy, chemotherapy and hormonal therapy, while reducing or avoiding the toxicities and/or side effects associated with the conventional therapies.

2.3 IMiDs®

A number of studies have been conducted with the aim of providing compounds that can safely and effectively be used to treat diseases associated with abnormal production of TNF-α. See, e.g., Marriott, J. B., et al., *Expert Opin. Biol. Ther.* 1(4): 1-8 (2001); G. W. Muller, et al., *Journal of Medicinal Chemistry* 39(17): 3238-3240 (1996); and G. W. Muller, et al., *Bioorganic & Medicinal Chemistry Letters* 8: 2669-2674 (1998). Some studies have focused on a group of compounds selected for their capacity to potently inhibit TNF-α production by LPS stimulated PBMC. L. G. Corral, et al., *Ann. Rheum. Dis.* 58:(Suppl I) 1107-1113 (1999). These compounds, which are referred to as IMiDs® (Celgene Corporation) or Immunomodulatory Drugs, show not only potent inhibition of TNF-α but also inhibition of LPS induced monocyte IL1β and IL12 production. LPS induced IL6 is also inhibited by immunomodulatory compounds of the invention, albeit partially. These compounds are potent stimulators of LPS induced IL10. Id. Particular examples of IMiDs® include, but are not limited to, the substituted 2-(2,6-dioxopiperidin-3-yl)phthalimides and substituted 2-(2,6-dioxopiperidin-3-yl)-1-oxoisoindoles described in U.S. Pat. Nos. 5,635,517, 6,281,230 and 6,316,471, to G. W. Muller, et al.

3. SUMMARY OF THE INVENTION

This invention encompasses methods of treating, preventing or managing certain types of cancer, including primary and metastatic cancer, as well as cancers that are relapsed, refractory or resistant to conventional chemotherapy. In particular, methods of this invention encompass methods of treating, preventing or managing various forms of leukemias such as chronic lymphocytic leukemia, chronic myelocytic leukemia, acute lymphoblastic leukemia, acute myelogenous leukemia and acute myeloblastic leukemia, including leukemias that are relapsed, refractory or resistant.

The methods comprise administering to a patient in need of such treatment, prevention or management a therapeutically or prophylactically effective amount of an immunomodulatory compound of the invention, or a pharmaceutically acceptable salt, solvate, hydrate, stereoisomer, clathrate, or prodrug thereof. In a preferred embodiment, the immunomodulatory compound is used alone, that is without other chemotherapeutics.

In another methods of the invention, an immunomodulatory compound of the invention is administered in combination with a therapy conventionally used to treat, prevent or manage cancer. Examples of such conventional therapies include, but are not limited to, surgery, chemotherapy, radiation therapy, hormonal therapy, biological therapy, immunotherapy and combinations thereof.

This invention also encompasses pharmaceutical compositions, single unit dosage forms, and dosing regimens which comprise an immunomodulatory compound of the invention, or a pharmaceutically acceptable salt, solvate, hydrate, stereoisomer, clathrate, or prodrug thereof, and a second, or additional, active agent. Second active agents include specific combinations, or "cocktails," of drugs or therapy, or both.

The preferred compound to be used in the methods and composition is 3-(4-amino-1-oxo-1,3-dihydro-isoindol-2-yl)-piperidine-2,6-dione (Revlimid®).

4. BRIEF DESCRIPTION OF FIGURE

FIG. 1 shows a comparison of the effects of 3-(4-amino-1-oxo-1,3-dihydro-isoindol-2-yl)-piperidine-2,6-dione (Revlimid®) and thalidomide in inhibiting the proliferation of multiple myeloma (MM) cell lines in an in vitro study. The uptake of [$^3$H]-thymidine by different MM cell lines (MM.1S, Hs Sultan, U266 and RPMI-8226) was measured as an indicator of the cell proliferation.

5. DETAILED DESCRIPTION OF THE INVENTION

A first embodiment of the invention encompasses methods of treating, managing, or preventing cancer which comprises administering to a patient in need of such treatment, management or prevention a therapeutically or prophylactically effective amount of an immunomodulatory compound of the invention, or a pharmaceutically acceptable salt, solvate, hydrate, stereoisomer, clathrate, or prodrug thereof. In particular, methods of this invention encompass methods of treating, preventing or managing various forms of leukemias, including but not limited to, chronic lymphocytic leukemia, chronic myelocytic leukemia, acute lymphoblastic leukemia, acute myelogenous leukemia and acute myeloblastic leukemia. In one embodiment, the leukemia is refractory leukemia, relapsed leukemia or a leukemia that is resistant to chemotherapy other than an immunomodulatory compound of the invention.

In a separate and distinct embodiment of the invention, the immunomodulatory compound of the invention is administered in combination with another drug ("second active agent") or another therapy for treating, managing, or preventing cancer. Second active agents include small molecules and large molecules (e.g., proteins and antibodies), examples of which are provided herein, as well as stem cells or cord blood. Methods, or therapies, that can be used in combination with the administration of an immunomodulatory compound of the invention include, but are not limited to, surgery, blood transfusions, immunotherapy, biological therapy, radiation therapy, and other non-drug based therapies presently used to treat, prevent or manage cancer.

The invention also encompasses pharmaceutical compositions (e.g., single unit dosage forms) that can be used in methods disclosed herein. Particular pharmaceutical compositions comprise an immunomodulatory compound of the invention, or a pharmaceutically acceptable salt, solvate, hydrate, stereoisomer, clathrate, or prodrug thereof, and a second active agent.

5.1 Immunomodulatory Compounds

Compounds used in the invention include compounds that are racemic, stereomerically enriched or stereomerically pure. In some embodiments, pharmaceutically acceptable salts, solvates, hydrates, clathrates, and prodrugs thereof are included. Preferred compounds used in the invention are small organic molecules having a molecular weight less than about 1,000 g/mol, and are not proteins, peptides, oligonucleotides, oligosaccharides or other macromolecules.

As used herein and unless otherwise indicated, the terms "immunomodulatory compounds" and "IMiDs®" (Celgene Corporation) encompasses small organic molecules that markedly inhibit TNF-α, LPS induced monocyte IL1β and IL12, and partially inhibit IL6 production. Specific immunomodulatory compounds of the invention are discussed below.

In the most preferred embodiment, "an immunomodulatory compound of the invention" refers to 3-(4-amino-1-oxo-1,3-dihydro-isoindol-2-yl)-piperidine-2,6-dione (lenalidomide, also known as Revlimid® or Revimid®). The compound 3-(4-amino-1-oxo-1,3-dihydro-isoindol-2-yl)-piperidine-2,6-dione has the following chemical structure:

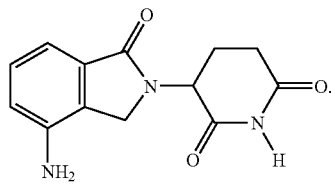

Specific examples of immunomodulatory compounds, include, but are not limited to, cyano and carboxy derivatives of substituted styrenes such as those disclosed in U.S. Pat. No. 5,929,117; 1-oxo-2-(2,6-dioxo-3-fluoropiperidine-3yl) isoindolines and 1,3-dioxo-2-(2,6-dioxo-3-fluoropiperidine-3-yl) isoindolines such as those described in U.S. Pat. No. 5,874,448; the tetra substituted 2-(2,6-dioxopiperdin-3-yl)-1-oxoisoindolines described in U.S. Pat. No. 5,798,368; 1-oxo and 1,3-dioxo-2-(2,6-dioxopiperidin-3-yl) isoindolines, including, but not limited to, those disclosed in U.S. Pat. No. 5,635,517; substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; a class of non-polypeptide cyclic amides disclosed in U.S. Pat. Nos. 5,698,579 and 5,877,200; thalidomide analogs, including hydrolysis products, metabolites, and precursors of thalidomide, such as those described in U.S. Pat. Nos. 5,593,990, 5,629,327, and 6,071,948 to D'Amato; and isoindole-imide compounds such as those described in U.S. patent publication no. 2003/0096841, and International Application No. PCT/US01/50401 (International Publication No. WO 02/059106). The entireties of each of the patents and patent applications identified herein are incorporated herein by reference. Immunomodulatory compounds of the invention do not include thalidomide.

The immunomodulatory compounds of the invention can either be commercially purchased or prepared according to the methods described in the patents or patent publications disclosed herein (see e.g., U.S. Pat. No. 5,635,517, incorporated herein by reference). Further, optically pure compounds can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the invention that comprise —NO, —NO₂, —ONO, or —ONO₂ moieties. Prodrugs can typically be prepared using well-known methods, such as those described in 1 *Burger's Medicinal Chemistry and Drug Discovery,* 172-178, 949-982 (Manfred E. Wolff ed., 5th ed. 1995), and *Design of Prodrugs* (H. Bundgaard ed., Elselvier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

The immunomodulatory compound of the invention contains a chiral center, and thus can exist as a racemic mixture of R and S enantiomers. This invention encompasses the use of stereomerically pure forms of this compound, as well as the use of mixtures of those forms. For example, mixtures comprising equal or unequal amounts of the enantiomers may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center. In other words, the invention encompasses the use of the R or S enantiomer of immunomodulatory compound in the methods.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.2 Second Active Agents

An immunomodulatory compound of the invention can be used with or combined with other pharmacologically active compounds ("second active agents") in methods and compositions of the invention. It is believed that certain combinations work synergistically in the treatment of particular types of cancers, and certain diseases and conditions associated with, or characterized by, undesired angiogenesis.

Immunomodulatory compounds of the invention can also work to alleviate adverse effects associated with certain second active agents, and some second active agents can be used to alleviate adverse effects associated with immunomodulatory compounds of the invention.

One or more second active ingredients or agents can be used in the methods and compositions of the invention together with an immunomodulatory compound of the invention. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful in this invention include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the invention include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

This invention encompasses the use of native, naturally occurring, and recombinant proteins. The invention further encompasses mutants and derivatives (e.g., modified forms)

of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with compounds of the invention include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. Compounds of the invention can also be combined with, or used in combination with, anti-TNF-α antibodies.

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits of the invention. See, e.g., Emens, L. A., et al., *Curr. Opinion Mol. Ther.* 3(1): 77-84 (2001).

In one embodiment of the invention, the large molecule active agent reduces, eliminates, or prevents an adverse effect associated with the administration of an immunomodulatory compound of the invention. Depending on the particular immunomodulatory compound of the invention and the disease or disorder begin treated, adverse effects can include, but are not limited to, drowsiness and somnolence, dizziness and orthostatic hypotension, neutropenia, infections that result from neutropenia, increased HIV-viral load, bradycardia, Stevens-Johnson Syndrome and toxic epidermal necrolysis, and seizures (e.g., grand mal convulsions). A specific adverse effect is neutropenia.

Second active agents that are small molecules can also be used to alleviate adverse effects associated with the administration of an immunomodulatory compound of the invention. However, like some large molecules, many are believed to be capable of providing a synergistic effect when administered with (e.g., before, after or simultaneously) an immunomodulatory compound of the invention. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethanine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O$^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

5.3 Methods of Treatments and Prevention

Methods of this invention encompass methods of treating, preventing or managing various types of cancers. In a preferred embodiment, methods of this invention encompass methods of treating, preventing or managing various types of leukemias such as chronic lymphocytic leukemia, chronic myelocytic leukemia, acute lymphoblastic leukemia, acute myelogenous leukemia, and acute myeloblastic leukemia.

As used herein, unless otherwise specified, the term "treating" refers to the administration of a compound of the invention, or other additional active agent, after the onset of symptoms of the particular disease or disorder. As used herein, unless otherwise specified, the term "preventing" refers to the administration prior to the onset of symptoms, particularly to patients at risk of cancer, and in particular leukemia. The term "prevention" includes the inhibition of a symptom of the particular disease or disorder. Patients with familial history of cancer or leukemia in particular are preferred candidates for preventive regimens. As used herein and unless otherwise indicated, the term "managing" encompasses preventing the recurrence of the particular disease or disorder in a patient who had suffered from it, lengthening the time a patient who had suffered from the disease or disorder remains in remission, and/or reducing mortality rates of the patients.

As used herein, the term "cancer" includes, but is not limited to, solid tumors and blood born tumors. The term "cancer" refers to disease of skin tissues, organs, blood, and vessels, including, but not limited to, cancers of the bladder, bone or blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

The various types of the cancers are described in U.S. provisional application No. 60/380,842, filed May 17, 2002, the entireties of which are incorporated herein by reference (see, e.g., Section 2.2. Types of Cancers). Specific cancers include, but are not limited to, leukemias such as chronic lymphocytic leukemia, chronic myelocytic leukemia, acute lymphoblastic leukemia, acute myelogenous leukemia, and acute myeloblastic leukemia; advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In one embodiment, the cancer is primary or metastatic. In another embodiment, the cancer is relapsed, refractory or resistance to chemotherapy or radiation; in particular, refractory to thalidomide. As used herein, the term "cancer" does not include myelodysplastic syndromes or MDS.

This invention encompasses methods of treating patients who have been previously treated for cancer, but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

Methods encompassed by this invention comprise administering one or more immunomodulatory compound of the invention, or a pharmaceutically acceptable salt, solvate, hydrate, stereoisomer, clathrate, or prodrug thereof, to a patient (e.g., a human) suffering, or likely to suffer, from cancer, particularly leukemia.

In one embodiment of the invention, an immunomodulatory compound of the invention can be administered orally and in single or divided daily doses in an amount of from about 0.10 to about 150 mg/day. In a preferred embodiment, 3-(4-amino-1-oxo-1,3-dihydro-isoindol-2-yl-piperidine-2,6-dione (Revlimid®) may be administered in an amount of from about 0.10 to 150 mg per day, from about 1 to about 50 mg per day, or from about 5 to about 25 mg per day. Specific doses per day include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a preferred embodiment, 3-(4-amino-1-oxo-1,3-dihydro-isoindol-2-yl-piperidine-2,6-dione (Revlimid®) may be administered in an amount of from about 1 to 50 mg per day, or from about 5 to about 25 mg per day to patients with various types of leukemias such as chronic lymphocytic leukemia, chronic myelocytic leukemia, acute lymphoblastic leukemia, acute myelogenous leukemia, and acute myeloblastic leukemia.

In particular, 3-(4-amino-1-oxo-1,3-dihydro-isoindol-2-yl-piperidine-2,6-dione (Revlimid®) may be administered to patients with chronic lymphocytic leukemia in an amount of from about 1 to 50 mg per day, or from about 5 to about 25 mg per day. In a specific embodiment, 3-(4-amino-1-oxo-1,3-dihydro-isoindol-2-yl-piperidine-2,6-dione (Revlimid®) may be administered to patients with chronic lymphocytic leukemia in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day. In a specific embodiment, Revlimid® can be administered in an amount of about 25 mg/day to patients with chronic lymphocytic leukemia.

In one embodiment, the recommended starting dose of 3-(4-amino1-oxo-1,3-dihydro-isoindol-2-yl)-piperidine-2,6-dione (Revlimid®) is 10 mg per day. The dose can be escalated every week to 15, 20, 25, 30, 35, 40, 45 and 50 mg/day. The patients who are dosed initially at 10 mg and who experience thrombocytopenia or neutropenia that develops within or after the first four weeks of starting Revlimid® therapy may have their dosage adjusted according to a platelet count or absolute neutrophil count (ANC).

5.3.1 Combination Therapy with a Second Active Agent

Specific methods of the invention comprise administering an immunomodulatory compound of the invention, or a pharmaceutically acceptable salt, solvate, hydrate, stereoisomer, clathrate, or prodrug thereof, in combination with one or more second active agents, and/or in combination with radiation therapy, blood transfusions, or surgery. Examples of immunomodulatory compounds of the invention are disclosed herein (see, e.g., section 5.1). Examples of second active agents are also disclosed herein (see, e.g., section 5.2).

Administration of an immunomodulatory compound of the invention and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for an immunomodulatory compound of the invention is orally. Preferred routes of administration for the second active agents or ingredients of the invention are known to those of ordinary skill in the art. See, e.g., *Physicians' Desk Reference*, 1755-1760 (56$^{th}$ ed., 2002).

In one embodiment of the invention, the second active agent is administered intravenously or subcutaneously and once or twice daily in an amount of from about 1 to about 1,000 mg, from about 5 to about 500 mg, from about 10 to about 375 mg, or from about 50 to about 200 mg. The specific amount of the second active agent will depend on the specific agent used, the type of disease being treated or managed, the severity and stage of disease, and the amount(s) of immunomodulatory compounds of the invention and any optional additional active agents concurrently administered to the patient. In a particular embodiment, the second active agent is rituximab, oblimersen (Genasense®), GM-CSF, G-CSF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In a specific embodiment, an immunomodulatory compound of the invention is administered in combination with rituximab to patients with leukemias. In a specific embodiment, Revlimid® is administered in an amount of from about 5 to about 25 mg per day to patients with chronic lymphocytic leukemia in combination with rituximab in an amount of 375 mg/m$^2$.

In another embodiment, an immunomodulatory compound of the invention is administered in combination with fludarabine, carboplatin, and/or topotecan to patients with refractory or relapsed or high-risk acute myelogenous leukemia.

In another embodiment, an immunomodulatory compound of the invention is administered in combination with liposomal daunorubicin, topotecan and/or cytarabine to patients with unfavorable karotype acute myeloblastic leukemia.

In another embodiment, an immunomodulatory compound of the invention is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In another embodiment, GM-CSF, G-CSF or EPO is administered subcutaneously during about five days in a four or six week cycle in an amount of from about 1 to about 750 mg/m$^2$/day, preferably in an amount of from about 25 to about 500 mg/m$^2$/day, more preferably in an amount of from about 50 to about 250 mg/m$^2$/day, and most preferably in an amount of from about 50 to about 200 mg/m$^2$/day. In a certain embodiment, GM-CSF may be administered in an amount of from about 60 to about 500 mcg/m$^2$ intravenously over 2 hours, or from about 5 to about 12 mcg/m$^2$/day subcutaneously. In a specific embodiment, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In a certain embodiment, EPO may be administered subcutaneously in an amount of 10,000 Unit 3 times per week.

This invention also encompasses a method of increasing the dosage of an anti-cancer drug or agent that can be safely and effectively administered to a patient, which comprises administering to a patient (e.g., a human) an immunomodulatory compound of the invention, or a pharmaceutically acceptable derivative, salt, solvate, clathrate, hydrate, or prodrug thereof. Patients that can benefit by this method are those likely to suffer from an adverse effect associated with anti-cancer drugs for treating a specific cancer of the blood, skin, subcutaneous tissue, lymph nodes, brain, lung, liver, bone, intestine, colon, heart, pancreas, adrenal, kidney, prostate, breast, colorectal, or combinations thereof. The administration of an immunomodulatory compound of the invention alleviates or reduces adverse effects which are of such severity that it would otherwise limit the amount of anti-cancer drug.

In one embodiment, an immunomodulatory compound of the invention can be administered orally and daily in an amount of from about 0.10 to about 150 mg, and preferably from about 1 to about 50 mg, more preferably from about 5 to about 25 mg prior to, during, or after the occurrence of the adverse effect associated with the administration of an anti-cancer drug to a patient. In a particular embodiment, an immunomodulatory compound of the invention is administered in combination with specific agents such as heparin, aspirin, coumadin, or G-CSF to avoid adverse effects that are associated with anti-cancer drugs such as but not limited to neutropenia or thrombocytopenia.

In another embodiment, this invention encompasses a method of treating, preventing and/or managing cancer, which comprises administering an immunomodulatory compound of the invention, or a pharmaceutically acceptable salt, solvate, hydrate, stereoisomer, clathrate, or prodrug thereof, in conjunction with (e.g., before, during, or after) conventional therapy including, but not limited to, surgery, immunotherapy, biological therapy, radiation therapy, or other non-drug based therapy presently used to treat, prevent or manage cancer. The combined use of the immunomodulatory compounds of the invention and conventional therapy may provide a unique treatment regimen that is unexpectedly effective in certain patients. Without being limited by theory, it is believed that immunomodulatory compounds of the invention may provide additive or synergistic effects when given concurrently with conventional therapy.

As discussed elsewhere herein, the invention encompasses a method of reducing, treating and/or preventing adverse or undesired effects associated with conventional therapy including, but not limited to, surgery, chemotherapy, radiation therapy, hormonal therapy, biological therapy and immunotherapy. An immunomodulatory compound of the invention and other active ingredient can be administered to a patient prior to, during, or after the occurrence of the adverse effect associated with conventional therapy.

In one embodiment, an immunomodulatory compound of the invention can be administered in an amount of from about 0.10 to about 150 mg, and preferably from about 1 to about 50 mg, more preferably from about 5 to about 25 mg orally and daily alone, or in combination with a second active agent disclosed herein (see, e.g., section 5.2), prior to, during, or after the use of conventional therapy.

5.3.2 Use with Transplantation Therapy

Compounds of the invention can be used to reduce the risk of Graft Versus Host Disease (GVHD). Therefore, the invention encompasses a method of treating, preventing and/or managing cancer, which comprises administering the immunomodulatory compound of the invention, or a pharmaceutically acceptable salt, solvate, hydrate, stereoisomer, clathrate, or prodrug thereof, in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of the immunomodulatory compound of the invention and transplantation therapy provides a unique and unexpected synergism. In particular, an immunomodulatory compound of the invention exhibits immunomodulatory activity that may provide additive or synergistic effects when given concurrently with transplantation therapy in patients with cancer.

An immunomodulatory compound of the invention can work in combination with transplantation therapy reducing complications associated with the invasive procedure of transplantation and risk of GVHD. This invention encompasses a method of treating, preventing and/or managing cancer which comprises administering to a patient (e.g., a human) an immunomodulatory compound of the invention, or a pharmaceutically acceptable salt, solvate, hydrate, stereoisomer, clathrate, or prodrug thereof, before, during, or after the transplantation of umbilical cord blood, placental blood, peripheral blood stem cell, hematopoietic stem cell preparation or bone marrow. Examples of stem cells suitable for use in the methods of the invention are disclosed in U.S. patent publication nos. 2002/0123141, 2003/0235909 and 2003/0032179, by R. Hariri et al., the entireties of which are incorporated herein by reference.

In one embodiment of this method, an immunomodulatory compound of the invention is administered to patients with leukemias before, during, or after the transplantation of autologous peripheral blood progenitor cell.

In another embodiment, an immunomodulatory compound of the invention is administered to patients with relapsed leukemia after the stem cell transplantation.

5.3.3 Cycling Therapy

In certain embodiments, the prophylactic or therapeutic agents of the invention are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment of the invention, an immunomodulatory compound of the invention is administered daily in a single or divided doses in a four to six week cycle with a rest period of about a week or two weeks. The invention further allows the frequency, number, and length of dosing cycles to be increased. Thus, another specific embodiment of the invention encompasses the administration of an immunomodulatory compound of the invention for more cycles than are typical when it is administered alone. In yet another specific embodiment of the invention, an immunomodulatory compound of the invention is administered for a greater number of cycles that would typically cause dose-limiting toxicity in a patient to whom a second active ingredient is not also being administered.

In one embodiment, an immunomodulatory compound of the invention is administered daily and continuously for three or four weeks at a dose of from about 0.10 to about 150 mg/d followed by a break of one or two weeks. In a particular embodiment, an immunomodulatory compound of the invention is administered in an amount of from about 1 to about 50 mg/day, preferably in an amount of about 25 mg/day for three to four weeks, followed by one week or two weeks of rest in a four or six week cycle.

In a preferred embodiment, 3-(4-amino-oxo-1,3-dihydro-isoindol-2-yl)-piperidine-2,6-dione (Revlimid®) is administered to patients with leukemia in an amount of from about 0.10 to about 150 mg per day for 21 days followed by seven days rest in a 28 day cycle. In the most preferred embodiment, 3-(4-amino-oxo-1,3-dihydro-isoindol-2-yl)-piperidine-2,6-dione (Revlimid®) is administered to patients with refractory or relapsed chronic lymphocytic leukemia in an amount of about 25 mg per day for 21 days followed by seven days rest in a 28 day cycle.

In one embodiment of the invention, an immunomodulatory compound of the invention and a second active ingredient are administered orally, with administration of an immunomodulatory compound of the invention occurring 30 to 60 minutes prior to a second active ingredient, during a cycle of four to six weeks. In another embodiment of the invention, an immunomodulatory compound of the invention is administered orally and a second active ingredient is administered by intravenous infusion.

In a specific embodiment, one cycle comprises the administration of from about 10 to about 25 mg/day of Revlimid® and from about 50 to about 750 mg/m$^2$/day of a second active ingredient daily for three to four weeks and then one or two weeks of rest. In a preferred embodiment, rituximab can be administered in an amount of 375 mg/m$^2$ as an additional active agent to patients with refractory or relapsed chronic lymphocytic leukemia. Typically, the number of cycles during which the combinatorial treatment is administered to a patient will be from about one to about 24 cycles, more typically from about two to about 16 cycles, and even more typically from about four to about three cycles.

5.4 Pharmaceutical Compositions and Dosage Forms

Pharmaceutical compositions can be used in the preparation of individual, single unit dosage forms. Pharmaceutical compositions and dosage forms of the invention comprise an immunomodulatory compound of the invention, or a pharmaceutically acceptable salt, solvate, hydrate, stereoisomer, clathrate, or prodrug thereof. Pharmaceutical compositions and dosage forms of the invention can further comprise one or more excipients.

Pharmaceutical compositions and dosage forms of the invention can also comprise one or more additional active ingredients. Consequently, pharmaceutical compositions and dosage forms of the invention comprise the active ingredients disclosed herein (e.g., an immunomodulatory compound of the invention and a second active agent). Examples of optional second, or additional, active ingredients are disclosed herein (see, e.g., section 5.2).

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges;

dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise an immunomodulatory compound of the invention or a pharmaceutically acceptable salt, solvate, hydrate, stereoisomer, clathrate, or prodrug thereof in an amount of from about 0.10 to about 150 mg. Typical dosage forms comprise an immunomodulatory compound of the invention or a pharmaceutically acceptable salt, solvate, hydrate, stereoisomer, clathrate, or prodrug thereof in an amount of about 0.1, 1, 2.5, 5, 7.5, 10, 12.5, 15, 17.5, 20, 25, 50, 100, 150 or 200 mg. In a specific embodiment, a preferred dosage form comprises 3-(4-amino-1-oxo-1,3-dihydro-isoindol-2-yl)-piperidine-2,6-dione (Revlimid®) in an amount of about 1, 2.5, 5, 10, 15, 20, 25 or 50 mg. Typical dosage forms comprise the second active ingredient in an amount of 1 to about 1000 mg, from about 5 to about 500 mg, from about 10 to about 350 mg, or from about 50 to about 200 mg. Of course, the specific amount of the anti-cancer drug will depend on the specific agent used, the type of cancer being treated or managed, and the amount(s) of an immunomodulatory compound of the invention and any optional additional active agents concurrently administered to the patient.

5.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

In one embodiment, a preferred dosage form is a capsule or tablet comprising 3-(4-amino-1-oxo-1,3-dihydro-isoindol-2-yl)-piperidine-2,6-dione (Revlimid®) in an amount of about 1, 2.5, 5, 10, 15, 20, 25 or 50 mg. In a specific embodiment, a preferred capsule or tablet dosage form comprises 3-(4- amino-1-oxo-1,3-dihydro-isoindol-2-yl)-piperidine-2,6-dione (Revlimid®) in an amount of about 5 or 10 mg.

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an immunomodulatory compound of the invention, anhydrous lactose, microcrystalline cellulose, polyvinylpyrrolidone, stearic acid, colloidal anhydrous silica, and gelatin.

5.4.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of an immunomodulatory compound of the invention and its derivatives. See, e.g., U.S. Pat. No. 5,134,127, which is incorporated herein by reference.

5.4.4 Topical and Mucosal Dosage Forms

Topical and mucosal dosage forms of the invention include, but are not limited to, sprays, aerosols, solutions, emulsions, suspensions, eye drops or other ophthalmic preparations, or other forms known to one of skill in the art. See, e.g., Remington's Pharmaceutical Sciences, $16^{th}$ and $18^{th}$ eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, $16^{th}$ and $18^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

6. EXAMPLES

Certain embodiments of the invention are illustrated by the following non-limiting example.

6.1 Toxicology Studies

The effects of 3-(4-amino-1-oxo-1,3-dihydro-isoindol-2-yl)-piperidine-2,6-dione (Revlimid®) on cardiovascular and respiratory function are investigated in anesthetized dogs. Two groups of Beagle dogs (2/sex/group) are used. One group receives three doses of vehicle only and the other receives three ascending doses of 3-(4-amino-1-oxo-1,3-dihydro-isoindol-2-yl)-piperidine-2,6-dione (2, 10, and 20 mg/kg). In all cases, doses of 3-(4-amino-1-oxo-1,3-dihydro-isoindol-2-yl)-piperidine-2,6-dione or vehicle are successively administered via infusion through the jugular vein separated by intervals of at least 30 minutes.

The cardiovascular and respiratory changes induced by 3-(4-amino-1-oxo-1,3-dihydro-isoindol-2-yl)-piperidine-2,6-dione are minimal at all doses when compared to the vehicle control group. The only statistically significant difference between the vehicle and treatment groups is a small increase in arterial blood pressure (from 94 mmHg to 101 mmHg) following administration of the low dose of 3-(4-amino-1-oxo-1,3-dihydro-isoindol-2-yl)-piperidine-2,6-dione. This effect lasts approximately 15 minutes and is not seen at higher doses. Deviations in femoral blood flow, respiratory parameters, and Qtc interval are common to both the control and treated groups and are not considered treatment-related.

6.2 Clinical Studies in Patients 6.2.1 Treatment of Chronic Lymphocytic Leukemia 3-(4-Amino-1-oxo-1,3-dihydro-isoindol-2-yl)-piperidin-2,6-dione (Revlimid®) was orally administered to patients with refractory or relapsed chronic lymphocytic leukemia (CLL) in an amount of 25 mg per day for 21 days followed by seven days rest on a 28 day cycle. Twenty seven patients of median age of 64 years (range: 47-75) were enrolled. Seventeen patients had Stage III or IV disease. Absolute lymphocyte counts were measured at Day 0, 7 and 30. Response was assessed at day 30 and monthly thereafter using the NCI-WG 1996 criteria. Patients with stable disease or better response were continued on therapy for a maximum of 12 months while those with progressive disease received rituximab (375 mg/m²) added to Revlimid®. Patients were considered evaluable for response if they completed at least two months of treatment.

All patients were available for toxicity and 13 out of 18 patients available for response evaluation. Nine patients on treatment were early for response assessment. Five patients achieved complete response and four patients achieved partial response. Three patients achieved stable disease (continued on treatment). Overall response rate in the 13 evaluable patients was 69%, while objective response rate defined as (complete response, partial response and stable disease) was 92.3%. Only one patient had progressive disease after three months of treatment.

Toxicity profile was predictable and manageable. Flare reaction (e.g., tender swelling of lymph nodes, sinus congestion and/or rash) was the common side effects noted. Other side effects were tumor lysis syndrome, grade 3/4 hematologic toxicities, and febrile neutropenia.

The study result shows that Revlimid® is effective in treating leukemia, particularly chronic lymphocytic leukemia.

6.2.2 Treatment of Relapsed Multiple Myeloma 4-(Amino)-2-(2,6-dioxo(3-piperidyl))-isoindoline-1,3-dione (Actimid™) was administered to patients with relapsed/refractory multiple myeloma. The study was conducted in compliance with Good Clinical Practices. Patients were at least 18 years old, had been diagnosed with multiple myeloma (with paraprotein in serum and/or urine), and were considered refractory to treatment after at least two cycles of treatment, or have relapsed after two cycles of treatment.

Patients who have progressive disease, according to the Southwest Oncology Group (SWOG) criteria, on their prior regimen are considered treatment refractory. Relapse following remission is defined as >25% increase in M component from baseline levels; reappearance of the M paraprotein that had previously disappeared; or a definite increase in the size and number of lytic bone lesions recognized on radiographs. Patients may have had prior therapy with thalidomide, provided they were able to tolerate the treatment. A Zubrod performance status of 0 to 2 is required for all patients.

4-(Amino)-2-(2,6-dioxo(3-piperidyl))-isoindoline-1,3-dione is administered to patients at doses of 1, 2, 5, or 10 mg/day for up to four weeks; at each dose level, three patients are initially enrolled. Dosing occurs at approximately the same time each morning; all doses are administered in the fasted state (no eating for at least two hours prior to dosing and two hours after dosing). 4-(Amino)-2-(2,6-dioxo(3-piperidyl))-isoindoline-1,3-dione doses are administered in an ascending fashion such that patients in the first cohort receive the lowest dose of 4-(amino)-2-(2,6-dioxo(3-piperidyl))-isoindoline-1,3-dione (1 mg/day) and escalation to the next higher dose level occurs only following the establishment of safety and tolerability at the current dose. If one out of three patients at any dose level experience dose limiting toxicity (DLT), three additional patients are enrolled at that dose. If none of the three additional patients experience DLT, escalation to the next dose level occurs; dose escalations continue in a similar fashion until the MTD is established or the maximum daily dose (10 mg/day) is attained. However, if one of the three additional patients enrolled experiences DLT, the MTD has been reached. If two or more of the three additional patients enrolled experience DLT, the MTD is judged to have been exceeded and three additional patients are enrolled at the preceding dose level to confirm the MTD. Once the MTD has been identified, four additional patients are enrolled at that dose level so that a total of 10 patients is treated at the MTD.

Blood sampling for analysis of pharmacokinetic parameters is performed on Days 1 and 28 according to the following sampling schedule: pre-dose, 0.25, 0.5, 0.75, 1, 1.5, 2, 2.5, 3, 4, 6, 8, 10, 12, 18, and 24 hours post-dose. An additional blood sample is collected at each weekly visit for the determination of 4-(amino)-2-(2,6-dioxo(3-piperidyl))-isoindoline-1,3-dione levels. Total urine collections are also made with urine pooled according to the following time intervals post-dose: 0 to 4, 4 to 8, 8 to 12, and 12 to 24 hours. Safety assessments are made by monitoring adverse events, vital signs, ECGs, clinical laboratory evaluations (blood chemistry, hematology, lymphocyte phenotyping, and urinalysis), and physical examination at specific times during the study.

Results of interim pharmacokinetic analyses obtained following single- and multiple-dose administration of 4-(amino)-2-(2,6-dioxo(3-piperidyl))-isoindoline-1,3-dione to multiple myeloma patients are presented below in Tables 1 and 2. These data show that 4-(amino)-2-(2,6-dioxo(3-piperidyl))-isoindoline-1,3-dione was steadily absorbed at all dose levels in relapsed multiple myeloma patients. Maximum plasma concentrations occurred at a median $T_{max}$ of between 2.5 and 2.8 hours post-dose at Day 1 and between 3 and 4 hours post-dose at Week 4. At all doses, plasma concentrations declined in a monophasic manner after reaching $C_{max}$. The start of the elimination phase occurred between 3 and 10 hours post-dose at Day 1 and Week 4, respectively.

These data also showed that after 4 weeks of dosing, 4-(amino)-2-(2,6-dioxo(3-piperidyl))-isoindoline-1,3-dione accumulated to a small extent (mean accumulation ratios ~1.02 to 1.52 and ~0.94 to 1.62 for $C_{max}$ and $AUC_{(0-\tau)}$, respectively). There was almost a dose proportional increase in $AUC_{(0-\tau)}$ and $C_{max}$ values with increasing dose. A five-fold higher dose of 4-(amino)-2-(2,6-dioxo(3-piperidyl))-isoindoline-1,3-dione produced a 3.2- and 2.2-fold increase in $C_{max}$ at Day 1 and Week 4, respectively. Similarly, a 5-fold increase in dose resulted in a 3.6- and 2.3-fold increase in $AUC_{(0-\tau)}$, at Day 1 and Week 4, respectively.

TABLE 1

Pharmacokinetic parameters of Actimid ™ in relapsed multiple myeloma patients

| Parameter | | 1 mg (N = 6) | 2 mg (N = 2) | 5 mg (N = 3) |
|---|---|---|---|---|
| Day 1 | | | | |
| $C_{max}$ | ng/mL | 15.03 (4.04) | 24.4* (12.1) | 48.56 (14.03) |
| $t_{max}$ | h | 3.3 (2.6) | 2.7* (0.3) | 2.3 (0.3) |
| $AUC_{(0-\infty)}$ | ng · h/mL | 152.90 (36.62) | 279.18 (51.10) | 593.10 (335.23) |
| $AUC_{(0-\tau)}$ | | 134.21 (27.14) | 249.57 (29.26) | 520.94 (267.32) |
| $t_{1/2}$ | h | 7.3 (3.4) | 6.3 (1.4) | 6.5 (2.2) |
| CL/F | mL/min | 114.75 (29.20) | 121.43 (22.22) | 182.31 (117.06) |
| Vz/f | L | 69.55 (44.97) | 65.31 (2.80) | 87.24 (22.61) |

*t = 24 hours
N/A = not available

TABLE 2

Pharmacokinetic parameters of Actimid ™ following multiple oral doses(1, 2, and 5 mg/day) in relapsed multiple myeloma patients

| Parameter | | 1 mg (N = 5) | 2 mg (N = 2) | 5 mg (N = 3) |
|---|---|---|---|---|
| | | Week 4 | | |
| $C_{max}$ | ng/mL | 23.20 (7.48) | 30.05* (15.64) | 58.07 (38.08) |
| $t_{max}$ | h | 3.6 (1.5) | 2.8* (0.3) | 5.0 (2.6) |
| $AUC_{(0-\infty)}$ | ng · h/mL | N/A | N/A | N/A |
| $AUC_{(0-\tau)}$ | | 239.31 (122.59) | 269.36 (186.34) | 597.24 (354.23) |
| $t^{1/2}$ | h | 6.2* (0.6) | 7.7 (2.8) | 7.8 (4.0) |
| CL/F | mL/min | 87.85 (48.48) | 162.68 (112.54) | 207.50 (175.41) |
| Vz/f | L | 41.35* (8.84) | 95.04 (35.39) | 103.95 (27.25) |

$\tau$ = 24 hours
N/A = not available
*N = 3 patients

6.2.3 Treatment of Relapsed Multiple Myeloma

Two Phase 1 clinical studies of 3-(4-amino-1-oxo-1,3-dihydro-isoindol-2-yl)-piperidine-2,6-dione (Revlimid®) have been conducted to identify the maximum tolerated dose (MTD) in patients with refractory or relapsed multiple myeloma. These studies have also characterized the safety profile of 3-(4-amino-1-oxo-1,3-dihydro-isoindol-2-yl)-piperidine-2,6-dione when ascending doses of 3-(4-amino-1-oxo-1,3-dihydro-isoindol-2-yl)-piperidine-2,6-dione were given orally for up to 4 weeks. Patients started 3-(4-amino-1-oxo-1,3-dihydro-isoindol-2-yl) -piperidine -2,6-dione treatment at 5 mg/day with subsequent escalation to 10, 25, and 50 mg/day. Patients were enrolled for 28 days at their assigned dose, with the option of extended treatment for those who did not exhibit disease progression or experience dose limiting toxicity (DLT). Patients were evaluated for adverse events at each visit and the severity of these events was graded according to the National Cancer Institute (NCI) Common Toxicity Criteria. Patients were discontinued if they experienced DLT (Grade 3 or greater non-hematological, or Grade 4 hematological toxicity).

In this study, 27 patients were enrolled. All patients had relapsed multiple myeloma and 18 (72%) were refractory to salvage therapy. Among these patients, 15 had undergone prior autologous stem cell transplantation and 16 patients had received prior thalidomide treatment. The median number of prior regimens was 3 (range 2 to 6).

Blood and urine samples were collected for analysis of pharmacokinetic parameters on Days 1 and 28. Blood samples were collected according to the following sampling schedule: pre-dose, 0.25, 0.5, 0.75, 1, 1.5, 2, 2.5, 3, 4, 6, 8, 10, 12, 18, and 24 hours post-dose. In addition, a blood sample was collected at each weekly clinic visit for 3-(4-amino-1-oxo-1,3-dihydro-isoindol-2-yl)-piperidine-2,6-dione determination. Total urine was collected and pooled according to the following time intervals post-dose: 0 to 4, 4 to 8, 8 to 12, and 12 to 24 hours. Response to treatment was assessed by M-protein quantification (by immunoelectrophoresis) from serum and a 24-hour urine collection, with creatinine clearance and 24-hour protein calculations undertaken at screening, baseline, Weeks 2 and 4, and monthly thereafter (or upon early termination). Bone marrow aspirations and/or tissue biopsy are also performed at Months 3, 6 and 12 if a patient's paraprotein serum concentration or 24-hour urine protein excretion declined to the next lower level, based on best response criteria. Preliminary results for the 28-day treatment period are summarized below.

Preliminary pharmacokinetic analyses based on these two studies indicated that AUC and $C_{max}$ values increase proportionally with dose following single and multiple doses in multiple myeloma patients (as was seen in healthy volunteers). Further, there was no evidence of accumulation with multiple dosing as single dose $AUC_{(0-\infty)}$ was comparable to multiple dose $AUC_{0-\tau}$ following the same dose of 3-(4-amino-1-oxo-1,3-dihydro-isoindol-2-yl)-piperidine-2,6-dione.

Similar to healthy volunteer studies, double peaks were observed. Exposure in multiple myeloma patients appeared to be slightly higher based on $C_{max}$ and AUC values as compared to healthy male volunteers while clearance in multiple myeloma patients was lower than it was in healthy volunteers, consistent with their poorer renal function (both as a consequence of their age and their disease). Finally, 3-(4-amino-1-oxo-1,3-dihydro-isoindol-2-yl)-piperidine-2,6-dione half-live in patients was shorter than in healthy volunteers (mean 8 hours, ranging up to 17 hours).

In this study, the first cohort of 3 patients was treated for 28 days at 5 mg/day without any dose limiting toxicity (DLT). The second cohort of 3 patients subsequently commenced therapy at 10 mg/day. Patients in the second 10 mg/day of 3-(4-amino-1-oxo-1,3-dihydro-isoindol-2-yl)-piperidine-2, 6-dione cohort tolerated treatment well.

6.2.4 Treatment of Relapsed or Refractory Multiple Myeloma

Patients with relapsed and refractory Dune-Salmon stage III multiple myeloma, who have either failed at least three previous regimens or presented with poor performance status, neutropenia or thrombocytopenia, are treated with up to four cycles of combination of melphalan (50 mg intravenously), an immunomodulatory compound of the invention (about 1 to 150 mg orally daily), and dexamethasone (40 mg/day orally on days 1 to 4) every four to six weeks. Maintenance treatment consisting of daily an immunomodulatory compound of the invention and monthly dexamethasone are continued until the disease progression. The therapy using an immunomodulatory compound of the invention in combination with melphalan and dexamethasone is highly active and generally tolerated in heavily pretreated multiple myeloma patients whose prognosis is otherwise poor.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating leukemia in a human, which comprises administering to a human having leukemia escalating doses of 3-(4-amino-1-oxo-1,3-dihydro-isoindol-2-yl)-piperidine-2,6-dione, wherein a starting dose is between about 2.5 mg/day and about 10 mg/day, and a maximum dose is between about 5 mg/day and about 50 mg/day, wherein the leukemia is chronic lymphocytic leukemia.

2. The method of claim 1, wherein the leukemia is relapsed, refractory or resistant to conventional therapy.

3. A method of treating leukemia in a human, which comprises administering to a human having leukemia escalating doses of 3-(4-amino-1-oxo-1,3-dihydro-isoindol-2-yl)-piperidine-2,6-dione, wherein a starting dose is between about 2.5 mg/day and about 10 mg/day, and a maximum dose is between about 5 mg/day and about 50 mg/day, and a therapeutically effective amount of a second active agent, wherein the leukemia is chronic lymphocytic leukemia.

4. The method of claim 3, wherein the second active agent is an antibody, hematopoietic growth factor, cytokine, anticancer agent, antibiotic, cox-2 inhibitor, immunomodulatory agent, immunosuppressive agent, or corticosteroid.

5. The method of claim 3, wherein the second active agent is rituximab, fludarabine, or a combination thereof.

6. The method of claim 5, wherein 3-(4-amino-oxo-1,3-dihydro-isoindol-2-yl)-piperidine-2,6-dione is administered after the administrations of rituximab and fludarabine.

7. The method of claim 1 or 3, wherein the maximum amount of 3-(4-amino-oxo-1,3-dihydro-isoindol-2-yl)-piperidine-2,6-dione administered is from about 5 to about 10 mg per day.

8. The method of claim 7, wherein the maximum amount of 3-(4-amino-oxo-1,3-dihydro-isoindol-2-yl)-piperidine-2,6-dione administered is about 10 mg per day.

9. The method of claim 1 or 3, wherein the maximum amount of 3-(4-amino-oxo-1,3-dihydro-isoindol-2-yl)-piperidine-2,6-dione administered is about 5, 6, 7, 8, 9, 10, 15, 20, or 50 mg per day.

10. The method of claim 1 or 3, wherein 3-(4-amino-oxo-1,3-dihydro-isoindol-2-yl)-piperidine-2,6-dione administered is enantiomerically pure.

11. The method of claim 10, wherein 3-(4-amino-oxo-1,3-dihydro-isoindol-2-yl)-piperidine-2,6-dione administered is S enantiomer.

12. The method of claim 10, wherein 3-(4-amino-oxo-1,3-dihydro-isoindol-2-yl)-piperidine-2,6-dione administered is R enantiomer.

13. The method of claim 1 or 3, wherein 3-(4-amino-oxo-1,3-dihydro-isoindol-2-yl)-piperidine-2,6-dione is administered in the form of a capsule or tablet.

14. The method of claim 1 or 3, wherein 3-(4-amino-oxo-1,3-dihydro-isoindol-2-yl)-piperidine-2,6-dione is administered in an amount of about 2.5 to 10 mg per day for 21 days followed by seven days rest in a 28 day cycle.

15. The method of claim 14, further comprising administration of rituximab in an amount of 375 mg/m$^2$.

16. The method of claim 1 or 3, wherein 3-(4-amino-oxo-1,3-dihydro-isoindol-2-yl)-piperidine-2,6-dione is administered orally.

17. The method of claim 1 or 3, wherein 3-(4-amino-oxo-1,3-dihydro-isoindol-2-yl)-piperidine-2,6-dione is administered in the form of a capsule.

18. The method of claim 17, wherein the 3-(4-amino-oxo-1,3-dihydro-isoindol-2-yl)-piperidine-2,6-dione is administered in the capsule of 5 mg, 10 mg, 15 mg, or 25 mg.

19. The method of claim 17, wherein the capsule comprises the 3-(4-amino-oxo-1,3-dihydro-isoindol-2-yl)-piperidine-2,6-dione, lactose anhydrous, microcrystalline cellulose, croscarmellose sodium and magnesium stearate.

20. The method of claim 1 or 3, wherein the starting dose of 3-(4-amino-1-oxo-1,3-dihydro-iusoindol-2-yl)-piperidine-2,6-dione is escalated each week.

21. The method of claim 1 or 3 wherein the starting dose of 3-(4-amino-1-oxo-1,3-dihydro-iusoindol-2-yl)-piperidine-2,6-dione is escalated every 28 days.

22. The method of claim 3 wherein the second active agent is dexamethasone, prednisone, or a combination thereof.

* * * * *